US011696962B2

(12) United States Patent
Moore

(10) Patent No.: US 11,696,962 B2
(45) Date of Patent: Jul. 11, 2023

(54) APPARATUS AND METHOD FOR DEPLOYING A PREOPERATIVE SKIN DISINFECTION DEVICE WITH INTEGRATED DRAPE

(71) Applicant: Mark R. Moore, Westlake, LA (US)

(72) Inventor: Mark R. Moore, Westlake, LA (US)

( * ) Notice: Subject to any disclaimer, the term of this patent is extended or adjusted under 35 U.S.C. 154(b) by 862 days.

(21) Appl. No.: 16/654,984

(22) Filed: Oct. 16, 2019

(65) Prior Publication Data
US 2021/0113721 A1 Apr. 22, 2021

(51) Int. Cl.
  *A61B 46/20* (2016.01)
  *A61B 90/40* (2016.01)
  *A61M 35/00* (2006.01)
  *A61L 2/00* (2006.01)
  *A61B 90/80* (2016.01)

(52) U.S. Cl.
  CPC .......... *A61L 2/0088* (2013.01); *A61B 46/20* (2016.02); *A61B 90/40* (2016.02); *A61B 90/80* (2016.02); *A61M 35/00* (2013.01); *A61B 2046/201* (2016.02); *A61L 2300/404* (2013.01)

(58) Field of Classification Search
  CPC ... A61B 46/20; A61B 2046/201; A61B 90/40; A61B 90/80; A61M 35/00; A61H 35/00; A61H 35/006
  See application file for complete search history.

(56) References Cited

U.S. PATENT DOCUMENTS

| 871,689 A | 11/1907 | Ganzhorn |
| 2,690,747 A | 10/1954 | Frallic |
| 3,327,705 A | 6/1967 | Spira et al. |
| 3,744,491 A | 7/1973 | Fischer |

(Continued)

FOREIGN PATENT DOCUMENTS

WO 2017216050 12/2017

OTHER PUBLICATIONS

Negosanti, Luca, Valentina Pinto, and Rossella Sgarzani. "Clinical evidences, personal experiences, recent applications." World Journal of Dermatology 1.3 (2012): 13-23.

(Continued)

*Primary Examiner* — Catharine L Anderson
*Assistant Examiner* — Lynne Anderson
(74) *Attorney, Agent, or Firm* — Schultz & Associates, P.C.

(57) ABSTRACT

A device is provided for enclosing an extremity of a patient for container efficient wound cleaning and for integrating draping prior to surgery. A loose-fitting flexible container with a flexible seal is provided for enclosing the extremity and treating the extremity in a controlled fashion to reduce or eliminate spillage and unwanted dispersion of antiseptic solution. Sealed to the flexible container is a vacuum packed, folded and rolled sterile surgical drape. The combination of a flexible container and a sterile pre-positioned surgical drape in a single device provides the advantage of controlled decontamination of the skin or wound while simultaneously providing the advantage of pre-positioning a surgical drape. The use of the device also provides the advantages of reduced operating room fires and biohazard dispersion risk and reduced cost by reduction of total operating room time per procedure.

15 Claims, 20 Drawing Sheets

(56) References Cited

U.S. PATENT DOCUMENTS

| | | |
|---|---|---|
| 4,376,437 A | 3/1983 | Sundheim et al. |
| 4,691,695 A | 9/1987 | Birk et al. |
| 4,772,259 A | 9/1988 | Frech et al. |
| 4,808,172 A | 2/1989 | Murata |
| 4,858,604 A | 8/1989 | Konishi |
| 5,029,579 A | 7/1991 | Trammell |
| 5,312,385 A | 5/1994 | Greco |
| 5,447,504 A | 9/1995 | Baker |
| 5,592,953 A | 1/1997 | Delao |
| 5,609,163 A | 3/1997 | Beard |
| 5,702,356 A | 12/1997 | Hathman |
| 5,769,806 A | 6/1998 | Radow |
| 5,823,977 A | 10/1998 | Dalyea |
| 5,848,998 A | 12/1998 | Marasco |
| 5,865,722 A | 2/1999 | Heng |
| 6,007,564 A | 12/1999 | Haverstock |
| 6,083,209 A | 7/2000 | Marasco |
| 6,241,697 B1 | 6/2001 | Augustine |
| 6,450,982 B1 | 9/2002 | Peterson |
| 6,562,013 B1 | 5/2003 | Marasco |
| 6,620,379 B1 | 9/2003 | Piuk et al. |
| 6,635,035 B1 | 10/2003 | Marasco |
| 6,664,434 B2 | 12/2003 | Cominsky |
| 6,992,233 B2 | 1/2006 | Drake et al. |
| 7,771,402 B2 | 8/2010 | Marasco |
| 8,048,044 B2 | 11/2011 | Stryker |
| 8,100,887 B2 | 1/2012 | Weston et al. |
| 8,158,844 B2 | 4/2012 | McNeil |
| 8,182,521 B2 | 5/2012 | Kane et al. |
| 8,206,363 B2 | 6/2012 | Bainbridge |
| 8,298,197 B2 | 10/2012 | Eriksson |
| 8,353,882 B1 | 1/2013 | Pelkus |
| 8,403,898 B2 | 3/2013 | Moore |
| 8,568,375 B2 | 10/2013 | Marasco |
| 8,603,150 B2 | 12/2013 | Kane et al. |
| 8,657,796 B2 | 2/2014 | Marasco |
| 8,679,050 B2 | 3/2014 | Nakamura |
| 8,708,998 B2 | 4/2014 | Weston et al. |
| 9,017,278 B2 | 4/2015 | Nakamura |
| 9,101,526 B2 | 8/2015 | Nakamura |
| 9,211,227 B2 | 12/2015 | Loori et al. |
| 9,579,431 B2 | 2/2017 | Buan et al. |
| 9,693,908 B2 | 7/2017 | Eriksson et al. |
| 10,004,884 B2 | 6/2018 | Allan et al. |
| 10,251,801 B2 * | 4/2019 | Breegi .................. A61B 90/30 |
| 2004/0171998 A1 | 9/2004 | Marasco |
| 2005/0043672 A1 | 2/2005 | Piuk et al. |
| 2011/0040239 A1 | 2/2011 | Schnieder et al. |
| 2011/0130712 A1 | 6/2011 | Topaz |
| 2011/0288458 A1 | 11/2011 | Jones et al. |
| 2012/0246820 A1 | 10/2012 | Huynh |
| 2014/0316455 A1 | 10/2014 | Gnanashanmugam |
| 2014/0343517 A1 | 11/2014 | Jameson |
| 2015/0119772 A1 | 4/2015 | Ruetenik |
| 2015/0119823 A1 | 4/2015 | Marasco |
| 2017/0007460 A1 | 1/2017 | Macdonald et al. |

OTHER PUBLICATIONS

Zhao, Jing-Chun, et al. "Hypertonic Glucose Combined with Negative Pressure Wound Therapy to Prepare Wounds with Pseudomonas aeruginosa Infection for Skin Grafting: A Report of 3 Cases." Ostomy/wound management 61.6 (2015): 28-44.

Amouzou, Komla S., et al. "Use of domestic negative pressure wound therapy in traumatic wounds for a cost-effective wound closure." Nigerian Journal of Plastic Surgery 13.2 (2017): 64.

* cited by examiner

APPARATUS AND METHOD FOR DEPLOYING A PREOPERATIVE SKIN DISINFECTION DEVICE WITH INTEGRATED DRAPE

FIELD OF THE INVENTION

This present invention relates to a device for cleaning, disinfecting and draping an extremity of a patient. A preferred embodiment of the invention provides a single combined device for isolating the extremity in sterile container which is integrated with a sterile surgical drape that is easily and quickly deployed.

BACKGROUND OF THE INVENTION

Since 1867, when Joseph Lister discovered the link between microbes and patient mortality after operations, he coined the term "antiseptic" after discovering that certain surgical preparations could be applied before surgery to eliminate bacteria. Practitioners have used aseptic techniques to reduce infections ever since.

Infections are frequently caused by bacteria commonly found in chronic wounds or on the surface of the skin. In order to reduce bacteria, antiseptics are applied to clean and disinfect the skin or open wounds prior to treatment or surgery. Types of antiseptics include alcohols, iodine or iodine-containing compounds and chlorhexidine gluconate among others.

One problem with common antiseptic solutions is that they include a large percentage of isopropyl alcohol. For example, a chlorhexidine antiseptic solution is typically 70% isopropyl alcohol. As the antiseptic solution evaporates the alcohol vapor becomes extremely flammable.

The most common technique used for disinfection of skin for presurgical incision requires painting and/or scrubbing of the antiseptic onto the skin with a sponge type applicator or gauze sponges. The disinfection of open wounds often requires emersion of the subject extremity in an antiseptic solution and then vigorously scrubbing to remove microbial colonies. Both of these disinfection techniques can be difficult to control because scrubbing often disperses the antiseptic solution over a wide area. Dispersion of flammable and caustic liquid onto nearby surfaces poses many problems, among them is the spreading of biohazardous material and creation of a fire hazard. Creation of a fire hazard is especially acute in the operating theater where pure oxygen is often used which can easily act as an accelerant to any fire created. Further, in in-home or outpatient cleaning procedures dispersion of antiseptic solution exacerbates cleaning problems and threat of biohazardous contamination.

Preoperative wound care and surgical site preparation present other challenges to the antiseptic cleaning process. For example, after cleaning, the extremity must be "draped" to isolate it from the surroundings. A "drape" is typically a waterproof sterile cloth including an opening or fenestration. The fenestration is positioned around the surgical site leaving the surgical site exposed.

Draping creates an area of asepsis as known as the sterile field. The sterile field is considered free of biological contaminants, thus allowing the surgical team to more closely approach the patient and the operating table prior to and during surgery.

Best practices require that the drape be placed on the patient in a controlled fashion. A drape that is positioned improperly must be replaced or covered before surgery can begin. Similarly, a drape that is dropped is considered nonsterile and must be completely replaced. Hence, the surgical draping procedure is often time consuming because it requires careful and correct positioning of the drape.

Many attempts have been made in the prior art to simplify wound cleaning, surgical cleaning and draping procedures.

One example of a draping procedure in the prior art is described in U.S. Pat. No. 3,910,268 to Miller. Miller discloses surgical drape for use in orthopedic surgery which is formed with two adjacent sections separated by an elongated slit or gap. A flap is created which, in use, is folded to overlap other portions of the drape in order to speed the draping procedure. However, Miller fails to provide a method of securing a drape around an extremity to prevent movement during surgery or to speed actual placement of the drape around the surgical site.

Another example is U.S. Pat. No. 3,750,664 to Collins. Collins discloses a surgical drape having a fenestration disposed adjacent the peripheral edges of the sheet. The fenestration may be molded into a contoured surface to prevent buckling or overlapping. However, Collins fails to disclose a method of cleaning the surgical site to prevent infection.

U.S. Pat. No. 3,791,381 to Crzewinski, discloses a surgical drape with a reinforced panel that may be cut to accommodate different surgical procedures. However, the folded drape provided by Crzewinski is difficult to deploy with a single nurse, thereby reducing its usefulness prior to surgery.

U.S. Pat. No. 5,222,507 to Taylor provides a surgical drape having a critical zone fixed to a main panel. A fenestration is formed by cutting through the critical zone. The critical zone is disclosed to be an absorbent material thereby largely eliminating the need for towels during surgery. However, the invention of Taylor fails to provide a method of securing the drape to the patient and so provides little if any time savings in the cleaning or draping procedures.

The prior art procedures for cleaning wounds and surgical sites and for surgical draping are all time consuming. The prior art cleaning techniques require clean-up time that slows the process. The time required by the draping procedure slows the throughput of the operating theater, thereby raising the cost of each operation. The prior art procedures for draping also put the patient at increased risk by lengthening the time under anesthesia.

The prior art procedures for cleaning wounds and surgical sites also fail to adequately address the problems created by the widespread dispersion and evaporation of the antiseptic solution and resulting cross contamination and fire hazard.

The prior art also fails to provide a combined method of isolating an extremity for cleaning and positioning a sterile surgical drape on the patient to increase cleaning and draping efficiency prior to surgery.

The current invention provides, among other things, a device which reduces dispersion of antiseptic solution during cleaning procedures thereby reducing the fire and cross contamination risks in both outpatient and inpatient procedures. The current invention also provides, among other things, a device and method for draping around a surgical site prior to surgery in a greatly reduced amount of time, thus reducing the time that the patient is under anesthesia and reducing per operation cost. The current invention also provides for a method of integrating the procedures of cleaning a surgical site and draping the extremity thereby reducing the amount of time required in the operating theater.

SUMMARY OF THE INVENTION

In a preferred embodiment, a device is provided which comprises a vacuum pack envelope subassembly combined with a sealed cleaning container for an extremity. The vacuum pack envelope subassembly contains a specially folded sterile surgical drape which includes a central opening or fenestration. The flexible container is attached to the base of the vacuum pack envelope subassembly and protrudes through the through central opening. In a preferred embodiment, the flexible container includes a resealable lateral closure and fluid ports which accommodate introduction of antiseptic solutions and manual cleaning of the surgical or wound site in a highly controlled fashion. The flexible container also includes a special rubberized seal having a central orifice that securely positions the extremity in the fenestration and seals the extremity inside the container. Both the flexible container and the vacuum pack envelope are enclosed in an openable outer bag to assure sterility of the drape and the flexible container prior to and during use.

When the device is used for cleaning, then the patient's extremity is placed through the orifice. Antiseptic is then introduced into the flexible container through a fluid port allowing the extremity to be immersed in antiseptic. Then, while the extremity is still sealed in the flexible container, it may be scrubbed to remove bacterial infestations. The antiseptic solution may then be drained from the flexible container and the device removed.

When the device is used prior to surgery, then both the cleaning procedure and draping procedure can be accomplished in an integrated fashion while maintaining both the sterility of the extremity and the sterility of the prepositioned drape.

Prior to surgery, the extremity is positioned in the flexible container and simultaneously in the fenestration. After controlled cleaning, the outer bag is opened to expose the flexible container and the vacuum pack envelope. The vacuum pack envelope is then opened and the surgical drape is deployed according to a novel deployment procedure. Remaining antiseptic is then drained from the flexible container in a controlled fashion using one or more of the fluid ports. The flexible container is then opened along lateral closures to provide access to the extremity for surgery.

A method of manufacturing a preferred embodiment of the device is also provided which includes, among other things, the steps of specially folding the surgical drape to be placed in the vacuum pack envelope subassembly, and then sealing the subassembly and evacuating it to eliminate the possibility of contamination and also reduce its size for ease of storage and use. The reduced size of the vacuum pack envelope also provides an indicator that the subassembly is sterile and ready for use. The subassembly is then assembled with and bonded to the flexible container so that the orifice of the container is substantially centered within the opening of the vacuum pack envelope subassembly and the fenestration of the surgical drape.

BRIEF DESCRIPTION OF THE DRAWINGS

In the detailed description of the preferred embodiments presented below, with reference being made to the accompanying drawings.

DETAILED DESCRIPTION OF THE INVENTION

Figure 1:
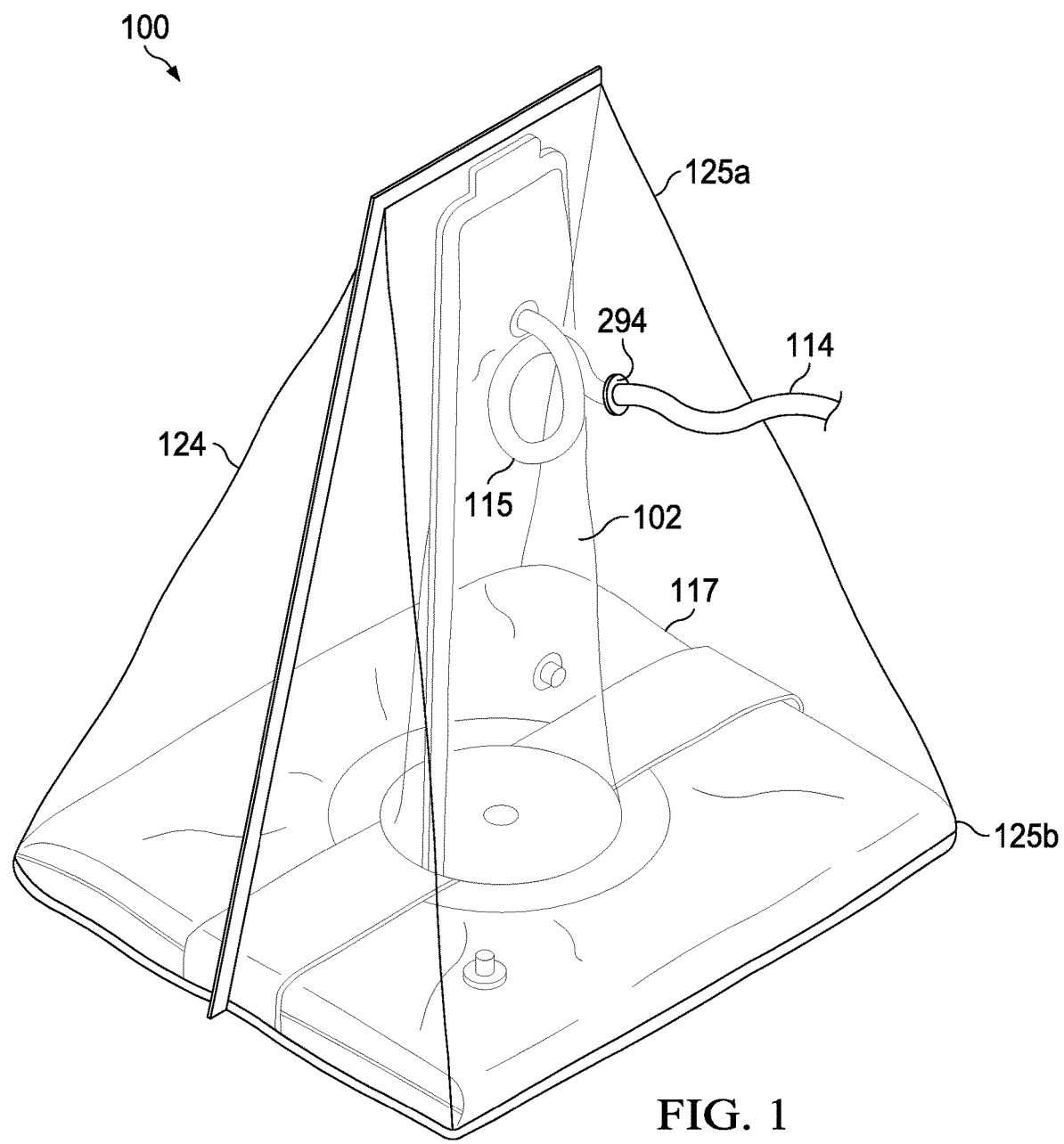
FIG. 1 is a perspective view of device in accordance with an embodiment of the invention.

Referring to FIG. 1, a preferred embodiment of device 100 comprises flexible container 102. Flexible container 102 is shown in an extended position, but may also be packaged in a collapsed position for compact storage. The flexible container can be made in many sizes to accommodate extremities of different sizes and for digits of these extremities such as fingers and toes. Flexible container 102 is bonded to a central opening in vacuum pack envelope subassembly 117. Flexible container 102 and vacuum pack envelope subassembly 117 are both enclosed in outer bag 124. The entire device, then, optionally, is contained in a sterile wrapper (not shown) for protection during shipping and handling of the device before use.

Antiseptic deployment tube 114 is provided between the outer bag and the flexible container, as will be further described. Pigtail 115 is provided in the deployment tube to allow free movement between the flexible container and the outer bag.

Figure 2:
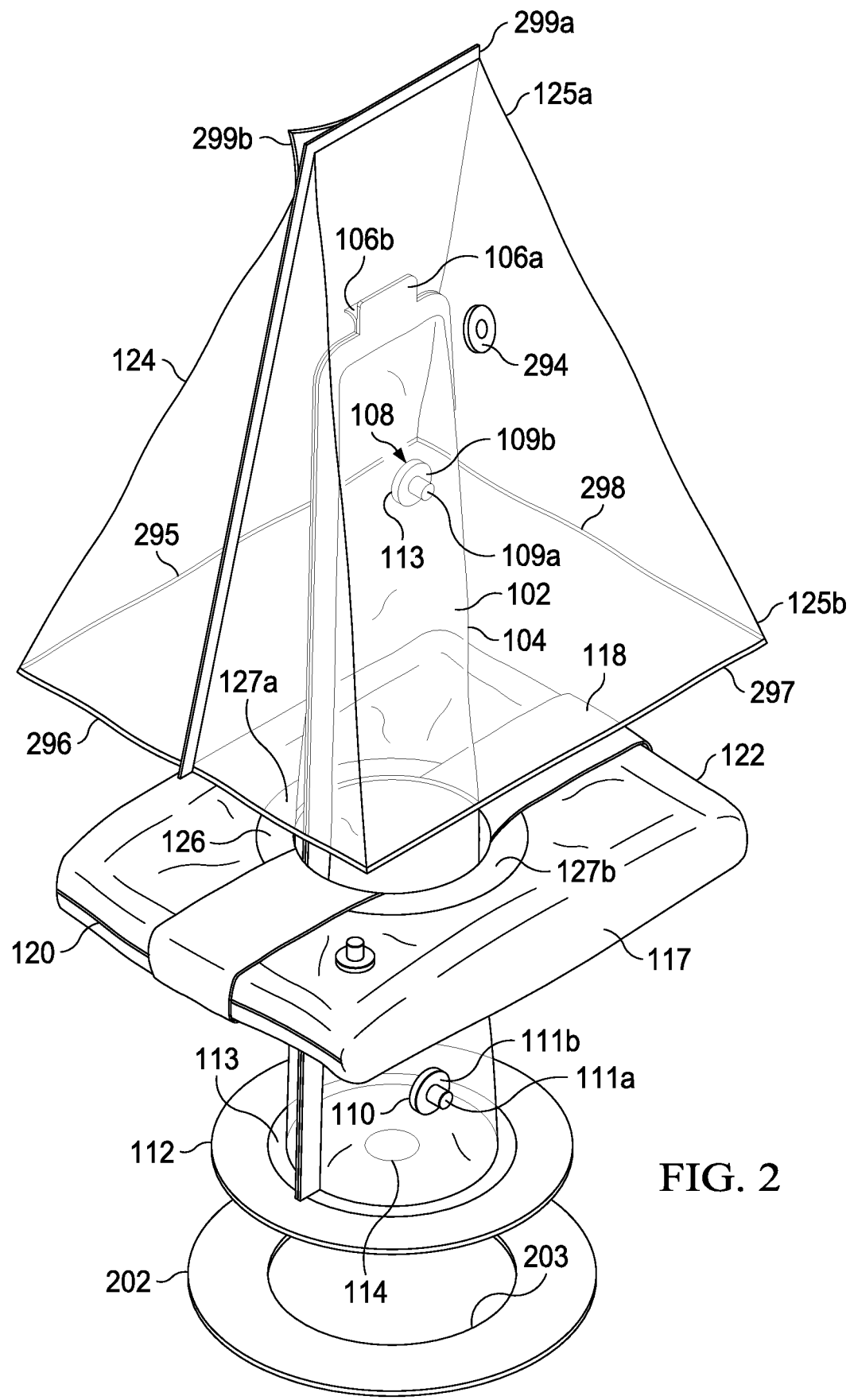
FIG. 2 is an exploded perspective view of a partially assembled device in accordance with one embodiment of the invention.

Referring to FIG. 2, an exploded view of the outer bag, flexible container and vacuum pack envelope subassembly will be further described.

Outer bag 124 forms a removable package for the vacuum pack envelope subassembly and the flexible container. In one embodiment, the outer bag forms elongated end 125a integrally formed with rectangular base 125b. Outer bag 124 includes lateral closures 299a and 299b. The lateral closures are Ziplock type mating closure. Outer bag 124 further comprises of releasable bonding surfaces 295, 296 and 297 and non-releasable bonding surface 298, which are used to attach the outer bag to the vacuum pack envelope. Flexible container 124 further includes through hole seal 294. The through hole seal forms a sealed connection around tube 114, as will be further described. In a preferred embodiment, outer bag 124 is a translucent polyethylene approximately 10 mils thick. However, other flexible materials may be employed so long as they are impervious to moisture and oxygen.

Flexible container 102 is comprised of a transparent, pliable, plastic bag bounded by seam 104 and mating lateral closures 106a and 106b. In a preferred embodiment, flexible container 102 is a polyethylene plastic approximately 2-10 mils thick. Seam 104 is preferably formed by an inductive weld. Lateral closures 106a and 106b are preferably "Ziploc" type mating closures which can be sealed, unsealed, and resealed allowing access to the interior of the flexible container. In another embodiment, a releasable adhesive can also be employed for the lateral closures.

Flexible container 102 further comprises distal fluid port 108 and proximal fluid port 110.

Distal fluid port 108 forms a ducted connection to the interior of the flexible container and further comprises cap 109a and threaded base 109b. Threaded base 109b is connected adjacent to a through hole (not shown) in flexible container 102. In use, cap 109a can be removed from threaded base 109b and replaced to allow for introduction or draining of an antiseptic solution, as will be further described.

Proximal fluid port 110 forms a ducted connection to the interior of the flexible container and further comprises cap 111a and threaded base 111b. Threaded base 111b is connected to a through hole (not shown) in flexible container 102. In use, cap 111a can be removed from threaded base 111b and replaced to allow for introduction or removal of an antiseptic solution, as will be further described.

In alternate embodiments, the fluid ports include integrally formed connectors which can be used to connect drain tubes, in a press fit fashion, as will be further described.

The flexible container is further bounded by flexible seal 112. Flexible seal 112 is preferably a circular flat, neoprene or rubber gasket approximately 2-20 mils thick. Flexible seal 112 includes centrally located orifice 114. In a preferred embodiment, the orifice is circular to effect even pressure on the exterior of the extremity when in use. Orifice 114 is used to surround a patient's extremity and secure it within the flexible container, as will be further described. Flexible container 102 is joined to flexible seal 112 adjacent the proximal ends of the lateral closures at connection interface 113. Connection interface 113 is preferably circular having a width of approximately 3 cm and is formed by an adhesive bond between the flexible seal and the interior of the flexible container. In a preferred embodiment, the adhesive is a permanent, nondegradable rubber cement 3M 1357 or 3M Super 77, available from 3M Corporation of Maplewood, Minn.

Lower collar 202 is bonded to the exterior of flexible seal 112 directly below connection interface 113. Lower collar 202 is generally circular and includes opening 203. Lower collar 202 in a preferred embodiment is a flexible polypropylene disk of approximately 20 mils thick. Lower collar 202 is bonded to flexible seal 112 with a permanent medical grade rubber adhesive, such as that already described.

Flexible container 102 protrudes through and is bonded to vacuum pack envelope subassembly 117, as will be further described.

Figure 3A:
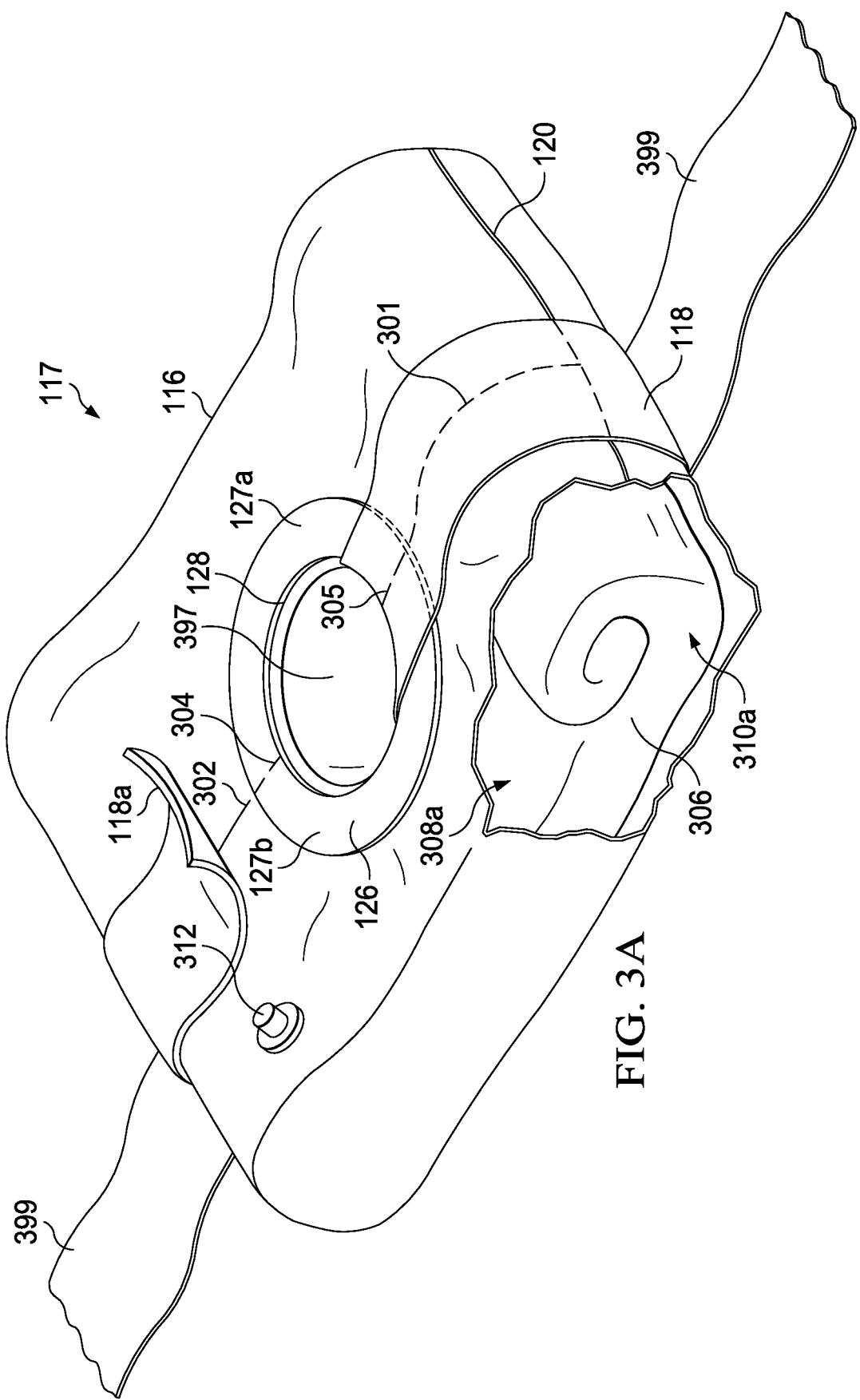
FIGS. 3A and 3B are cutaway and perspective views of the vacuum pack envelope subassembly in accordance with one embodiment of the invention.
Figure 3B:
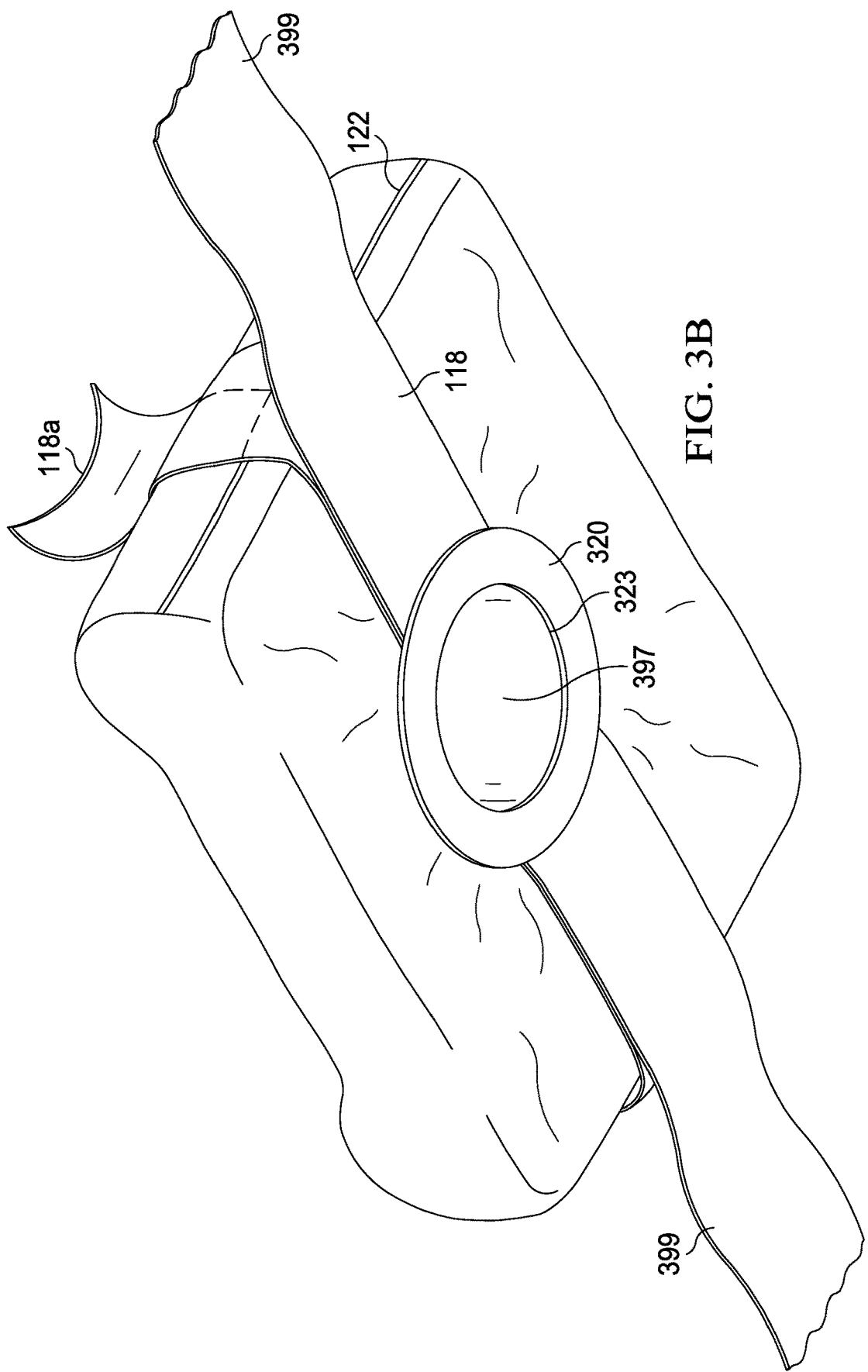

Referring then to FIGS. 3A and 3B, vacuum pack envelope subassembly 117 will be further described. Vacuum pack envelope subassembly 117 comprises openable envelope 116 which contains folded surgical drape 306. Preferably the envelope is comprised of polyethylene sheeting approximately 10-20 mils thick. Other materials capable of an airtight seal may be employed.

As shown in cut away, folded surgical drape 306 comprises two fan fold sections and two roll fold sections, fan fold section 308a and roll fold section 310a are shown as examples. The vacuum pack subassembly further includes centrally located circular composite opening 397, as will be further described. Other smooth surfaced openings such as ovals and ellipses are also contemplated. In a preferred embodiment, the surgical drape is formed in the shape of a rectangle, with each side approximately 3 meters in length and is made of polyethylene or spun polypropylene. The surgical drape may also include a tack surface on the bottom nonsterile side in order to aide in secure placement on the patient prior to surgery.

Vacuum pack envelope 116 includes longitudinal seal closures 301 and 302, and lateral seal closures 120 and 122. The longitudinal and lateral seal closures in a preferred embodiment are air tight resealable closures such as Ziplock type closures. In other embodiments, the closures may be inductively etched tear lines in the plastic surface. As can be seen, seal tape 118 covers the longitudinal seal closures and partially covers the lateral seal closures. The seal tape preferably is a polyethylene film comprised of one tacky side. Preferably the seal tape is 3M Adhesive Transfer Tape 9547, although other similar alternatives may be employed.

Bifurcated seal ring 126 is positioned on the top surface of the vacuum pack envelope. The bifurcated seal ring is a generally circular, flat disk and includes opening 128. Opening 128 is positioned around central opening 397. Bifurcated ring seal 126 is comprised of ring half 127a and ring half 127b. Ring halves 127a and 127b are integrally formed, but are separated by perforations 304 and 305, respectively. Perforations 304 and 305 are positioned directly adjacent longitudinal seal closures 301 and 302, respectively. The perforations serve as "break-lines" between the ring halves which allow for easy opening of the vacuum pack envelope during use. In a preferred embodiment, the bifurcated ring seal is made of a rigid polypropylene approximately 50 mils thick. The important purpose of the ring halves is to provide a secure way to grasp the vacuum pack envelope as it is being opened during use to prevent draping errors. A further purpose of the bifurcated seal ring and seal tape is to assure that the vacuum pack envelope has not been inadvertently opened and contaminated before use, and so further assures sterility of the surgical drape contained.

As shown in detail 118a, seal tape 118 may be peeled from the vacuum pack envelope thereby exposing the perforations in the bifurcated seal ring and the longitudinal and lateral seal closures.

Vacuum pack envelope 116 further comprises vacuum port 312. Vacuum port 312 is a self-sealing orifice which is ductedly connected with the interior of the vacuum pack envelope. The port allows evacuation of oxygen from the interior of the vacuum pack envelope in order to minimize contamination risk. In a preferred embodiment, the vacuum port may also allow the backfilling of the envelope with an inert gas, such as Argon, to promote sterility of the surgical drape.

Referring to FIG. 3B, seal tape 118 is bonded to middle collar 320. Middle collar 320 is generally circular and includes opening 323 which surrounds opening 397 in the vacuum pack envelope. In a preferred embodiment, middle collar 320 is formed of a semi rigid plastic material such as polypropylene or polystyrene approximately 50 mils thick. Also bonded to middle collar 320 is body strap 399. Body strap 399 is secured to an exterior surface of the seal tape, by a suitable waterproof semi-permanent adhesive, and is used to secure the vacuum pack envelope to the patient. In a preferred embodiment, body strap 399 is made of a non-stretchable medical grade laminate, including hook and loop closures, such as Rolyan Soft Strap, available from Sammons Preston.

Figure 4:
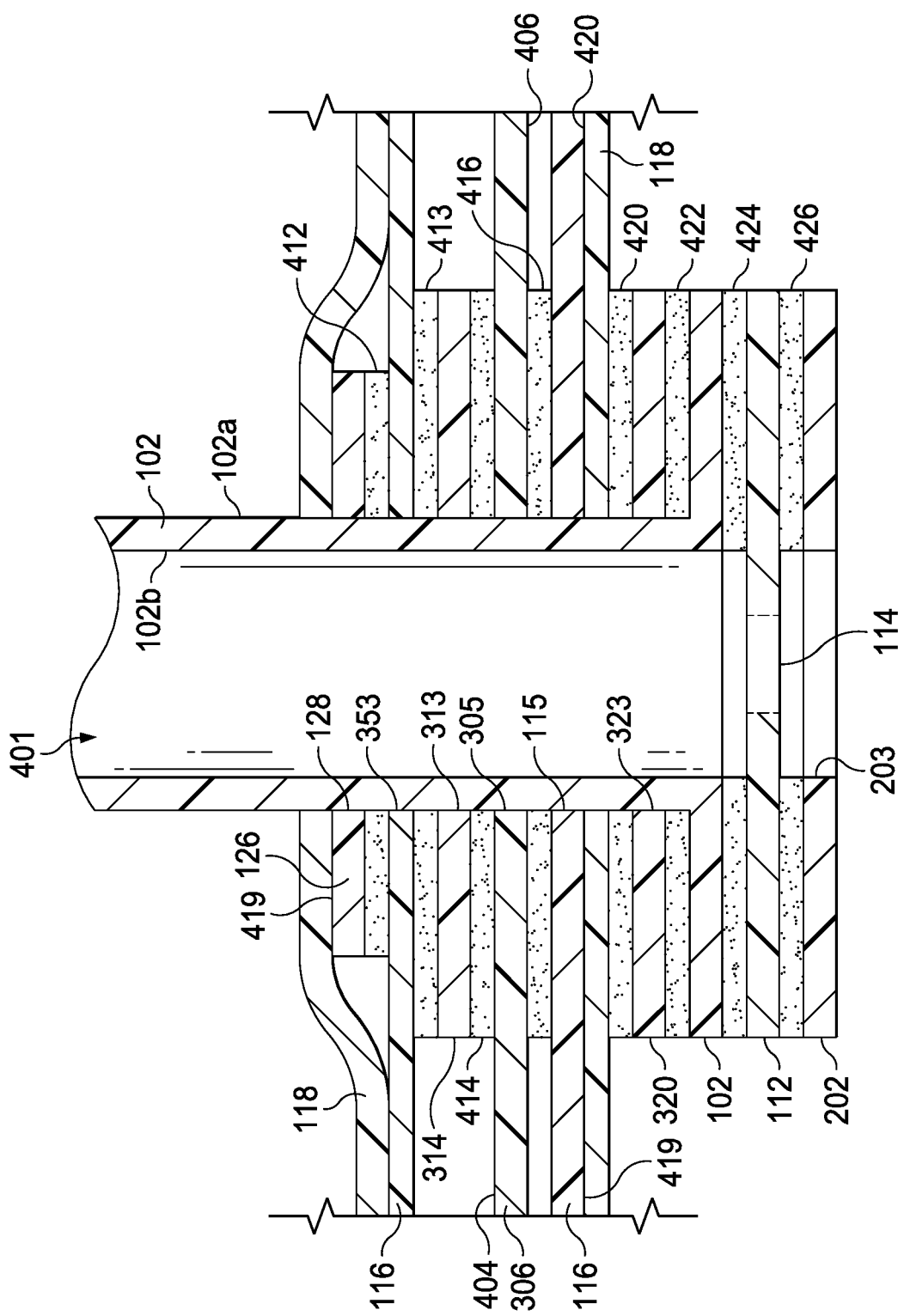
FIG. 4 is a cutaway view of a preferred embodiment of the invention.

Referring then to FIG. 4, a partial cut away view of a preferred structure for the device will be described.

Flexible container 102 is shown at the top of the figure in cutaway, extending downward and forming central chamber 401. Seal tape 118 is shown directly adjacent the exterior of flexible container 102.

Seal tape 118 is adhered to bifurcated seal ring 126 and the exterior of vacuum pack envelope 116 at tack surface 419. Tack surface 419 generally extends along the entire interior surface of seal tape 118. Bifurcated seal ring 126 includes opening 128 that is positioned adjacent flexible container 102 and is generally concentrically aligned with opening 305. Bifurcated seal ring 126 is adhered to the external surface of vacuum pack envelope 116 by permanent adhesive 412. Vacuum pack envelope 116 includes upper opening 353. Upper opening 353 is adjacent the exterior of flexible container 102 and is generally concentrically aligned with opening 305. Vacuum pack envelope 116 is adhered to upper collar 314 by a permanent rubber adhesive 413. Upper collar 314 includes opening 313. Opening 313 is adjacent the exterior of flexible container 102 and is generally concentrically aligned with opening 305.

Surgical drape 306 includes opening 305 adjacent the exterior of flexible container 102. Surgical drape 306 includes surface 404 and surface 406. Upper collar 314 is adhered to surface 404 by permanent rubber adhesive 414. Surface 406 is adhered to the interior surface of vacuum pack envelope 116 by permanent rubber adhesive 416. Vacuum pack envelope 116 includes lower opening 115. Lower opening 115 is adjacent the exterior of flexible container 102 and is generally concentrically aligned with opening 305.

The exterior surface of vacuum pack envelope 116 is adhered to the interior tack surface 419 of seal tape 118. Seal tape 118 is adhered to middle collar 320 by adhesive 420. Middle collar 320 includes opening 323. Opening 323 is adjacent the exterior of flexible container 102 and is generally concentrically aligned with opening 305. Adhesive 420 is a flexible, permanent, rubber adhesive, as previously described. Middle collar 320 is adhered to the exterior surface of flexible container 102 by adhesive 422. Adhesive 422 is a flexible, permanent, rubber adhesive, as previously described.

The interior surface of flexible container 102 is adhered to flexible seal 112 by adhesive 424. Flexible seal 112 includes orifice 114. Orifice 114 is generally concentrically aligned with opening 305. Adhesive 424 is a flexible, permanent, rubber adhesive, as previously described.

Flexible seal 112 is likewise adhered to lower collar 202, by adhesive 426. Lower collar 202 includes opening 203. Opening 203 is generally concentrically aligned with opening 305. Adhesive 426 is a flexible, permanent, rubber adhesive, as previously described.

As can be seen, the exterior surface of flexible container 102 further comprises exterior surface 102a and interior surface 102b. Exterior surface 102a contacts openings 128, 353, 313, 305, 115 and 323 and forms a barrier between central chamber 401 and the outside world. As can also be seen, in this embodiment, openings 128, 353, 313, 305, 115, 323 and 203 are all generally the same diameter. Similarly, these openings and orifice 114 are all generally concentric. The concentric alignment of the openings is important because it assures that interior surface 102b is smooth and free from aberrations which might interfere with insertion of a patient extremity during use.

Figure 5A:
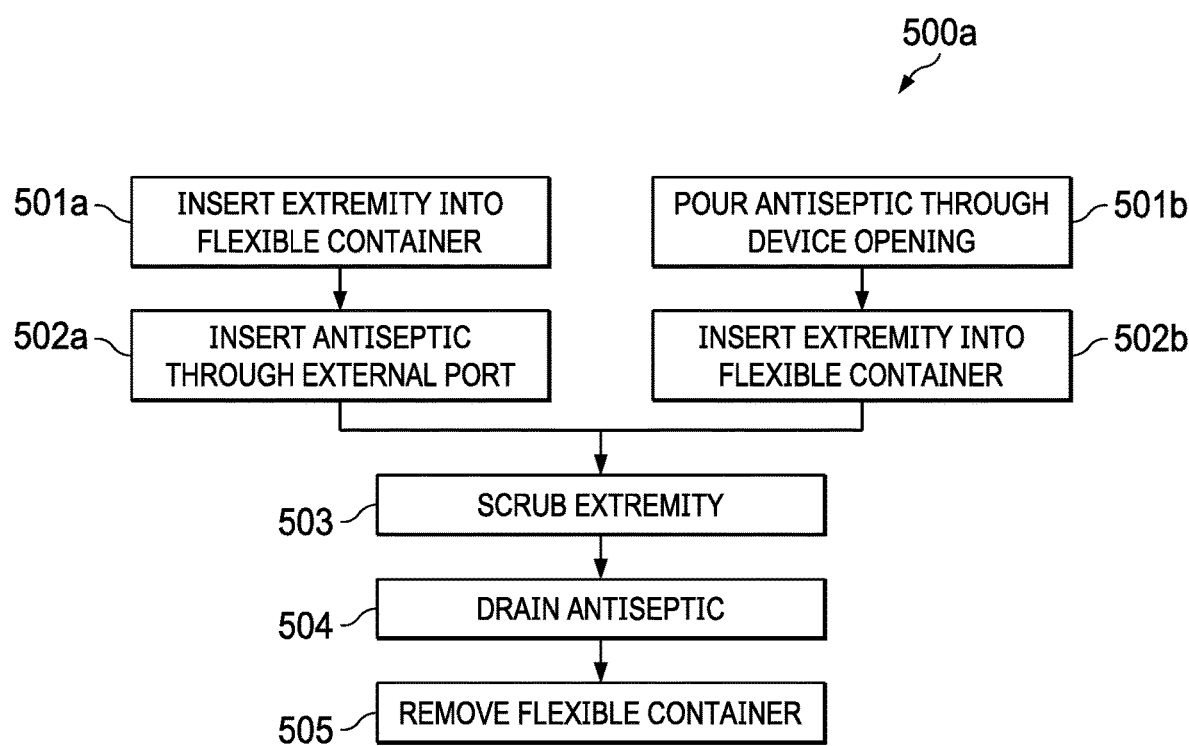
FIG. 5A is a flow chart of the steps required by a preferred method of use of the invention in a cleaning situation.
Figure 5B:
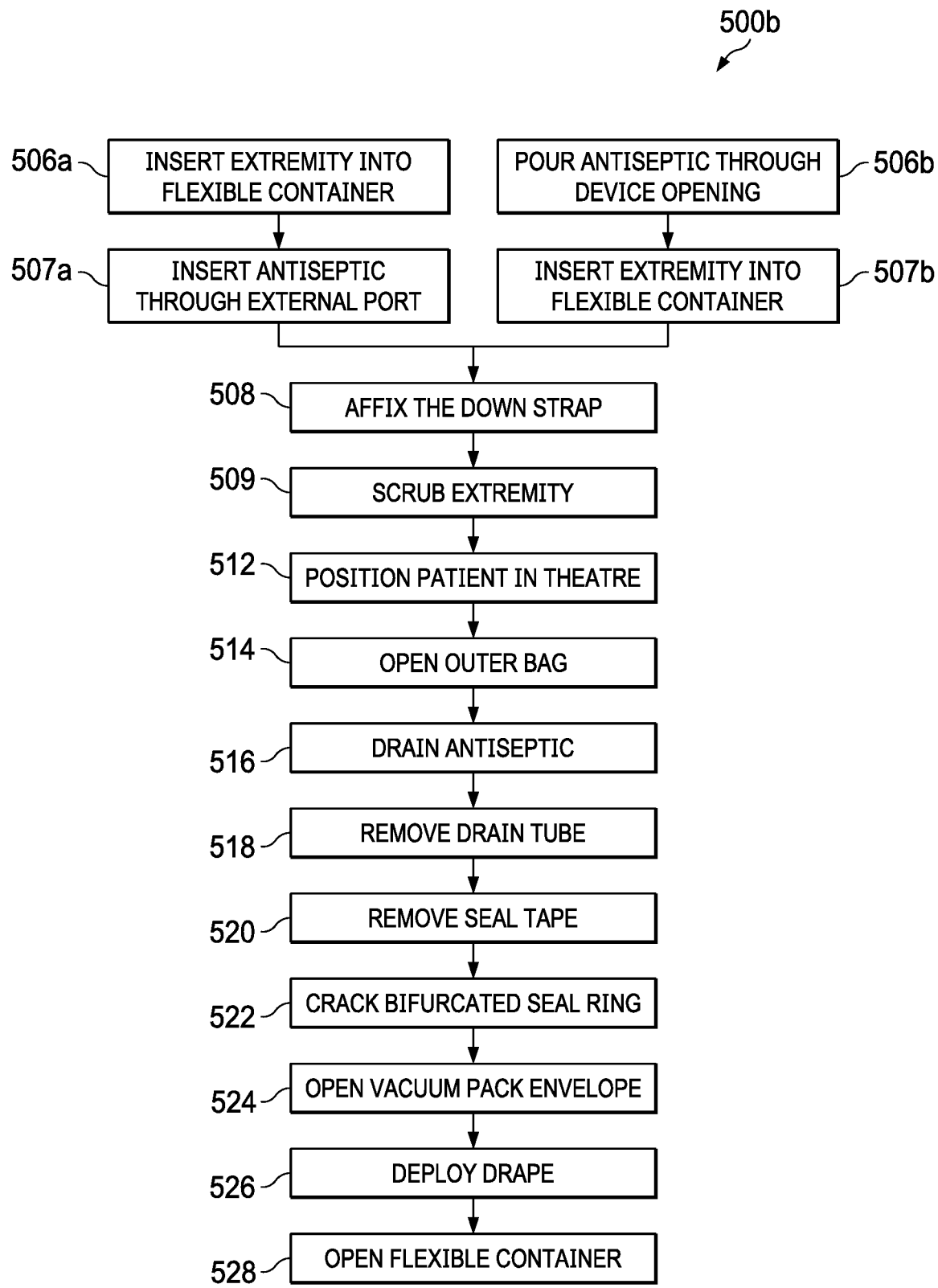
FIG. 5B is a flow chart of the steps required by a preferred method of use of the invention in an integrated cleaning and surgical situation.

Referring to FIG. 5A, preferred method 500a of using the device, will be described.

At step 501a, the extremity of the patient is inserted into the flexible container through orifice 114. Orifice 114 forms a moisture tight seal around the extremity.

At step 502a, an antiseptic solution is introduced into the flexible container through either distal fluid port 108 or proximal fluid port 110. After introducing the antiseptic solution, the fluid port is closed and sealed with the removable lid.

In an alternate embodiment, at step 501b, the antiseptic solution is introduced into the flexible container through one or more of the orifices. At step 502b, the extremity of the patient is then inserted into the flexible container through orifice 114, as previously described.

At step 503, the extremity is scrubbed to remove bacteria while remaining in the flexible container. At step 504, the antiseptic solution is drained from the flexible container through proximal fluid port or the distal fluid port (or both). At step 505, the flexible container is removed from the extremity.

Referring to FIGS. 5B and 6A-6E, a preferred method 500b of use of the device, will be described.

At step 506a, the extremity of the patient is inserted into the flexible container through orifice 114. Orifice 114 forms a moisture tight seal around the extremity and securely holds it within the flexible container centrally aligned with opening 305 of the surgical drape. The grip of the orifice on the extremity is important because it prevents rotation of the surgical drape about the axis of the extremity and also prevents movement of the surgical drape in a proximal or distal direction along the extremity.

At step 507a, an antiseptic solution is introduced into the flexible container through either distal fluid port 108 or proximal fluid port 110. After introducing the antiseptic solution, the fluid port is closed and sealed with the removable lid.

In an alternate embodiment, at step 506b an antiseptic solution is introduced into the flexible container through one or more of the orifices. At step 507b, the extremity of the patient is then inserted into the flexible container through orifice 114, as previously described.

At step 508, the Velcro tie down strap is deployed and placed around the patient and secured. The tie down strap assists in holding orifice 114 in place on the extremity in order to prevent escape of the antiseptic solution.

At step 509, the extremity is scrubbed to remove bacteria while remaining in the flexible container.

Steps 506a, 507a, 506b, 507b, 508 and 509 may be conducted in the operating theater, but may also be conducted outside it, thereby saving time in the operating theater and shortening the time that the patient is under anesthesia.

At step 512, if not already done so, the patient is positioned in the operating theater, on the operating table.

Figure 6A:
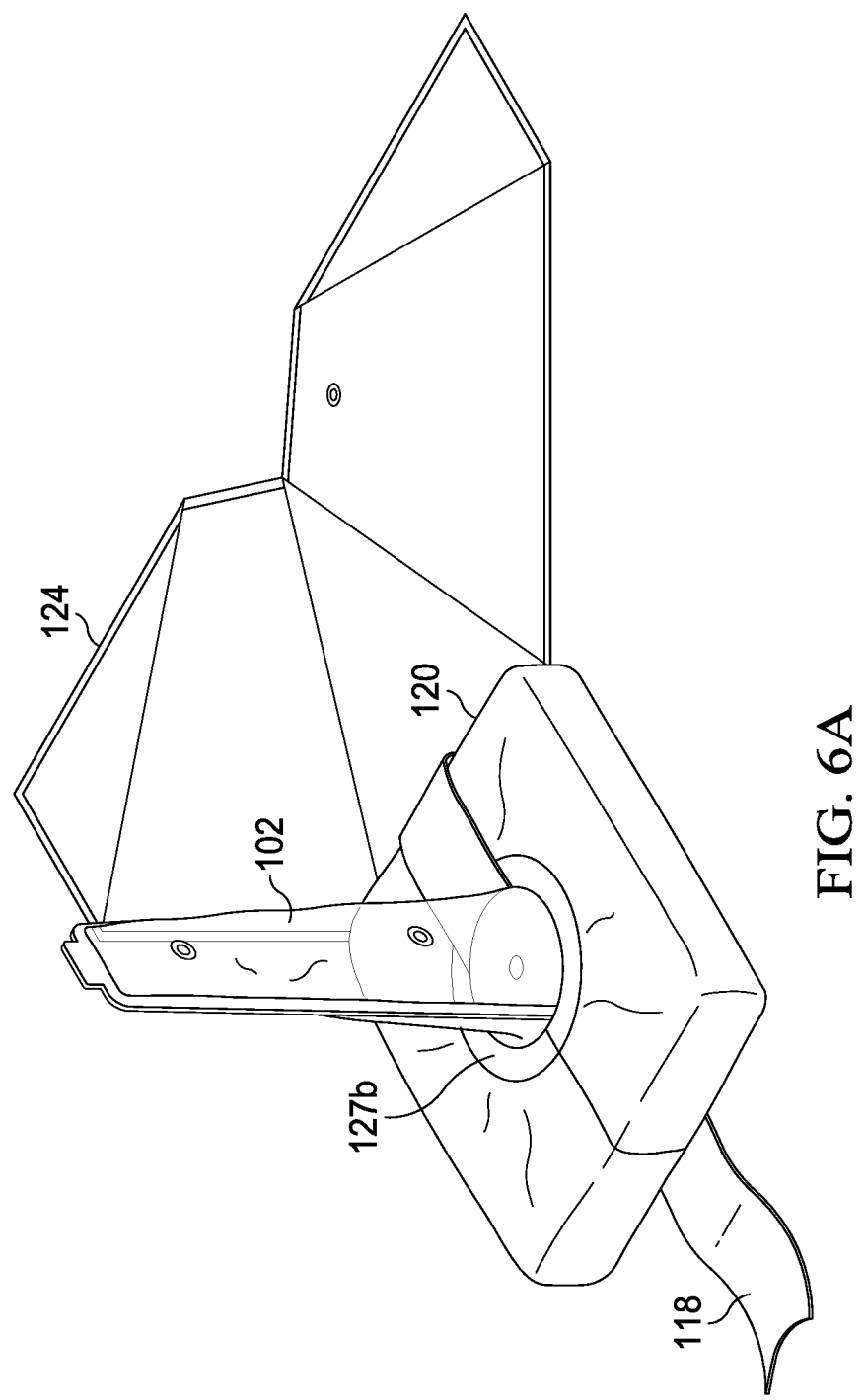
FIGS. 6A-6F show a preferred embodiment of the invention in use.

At step 514, lateral closures 299a and 299b are opened thereby exposing the exterior surface of the flexible container. Releasable bonding surfaces 295, 296 and 297 are then released from the vacuum pack envelope subassembly, as shown in FIG. 6A. The outer bag is then positioned under the extremity and on the operating table to form a sterile field, as will be further described.

At step 516, the antiseptic is drained from the flexible container through one or more of the ports, through the drain tube.

At step 518, the drain tube is removed from the flexible container.

At step 520, seal tape 118 is removed, exposing the longitudinal and lateral seal closures, and bifurcated seal ring 126, as shown in FIG. 6A.

Figure 6B:
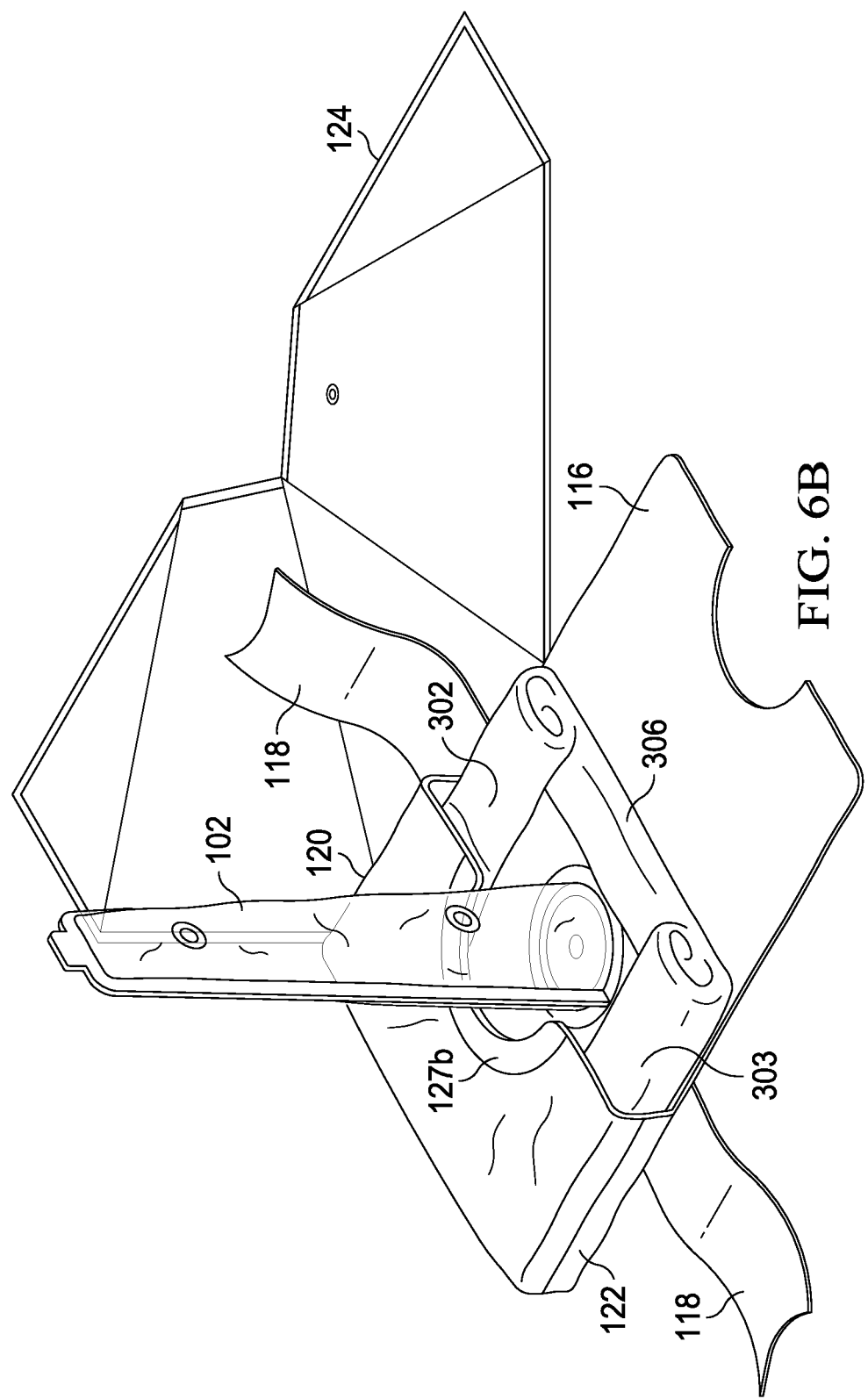
Figure 6C:
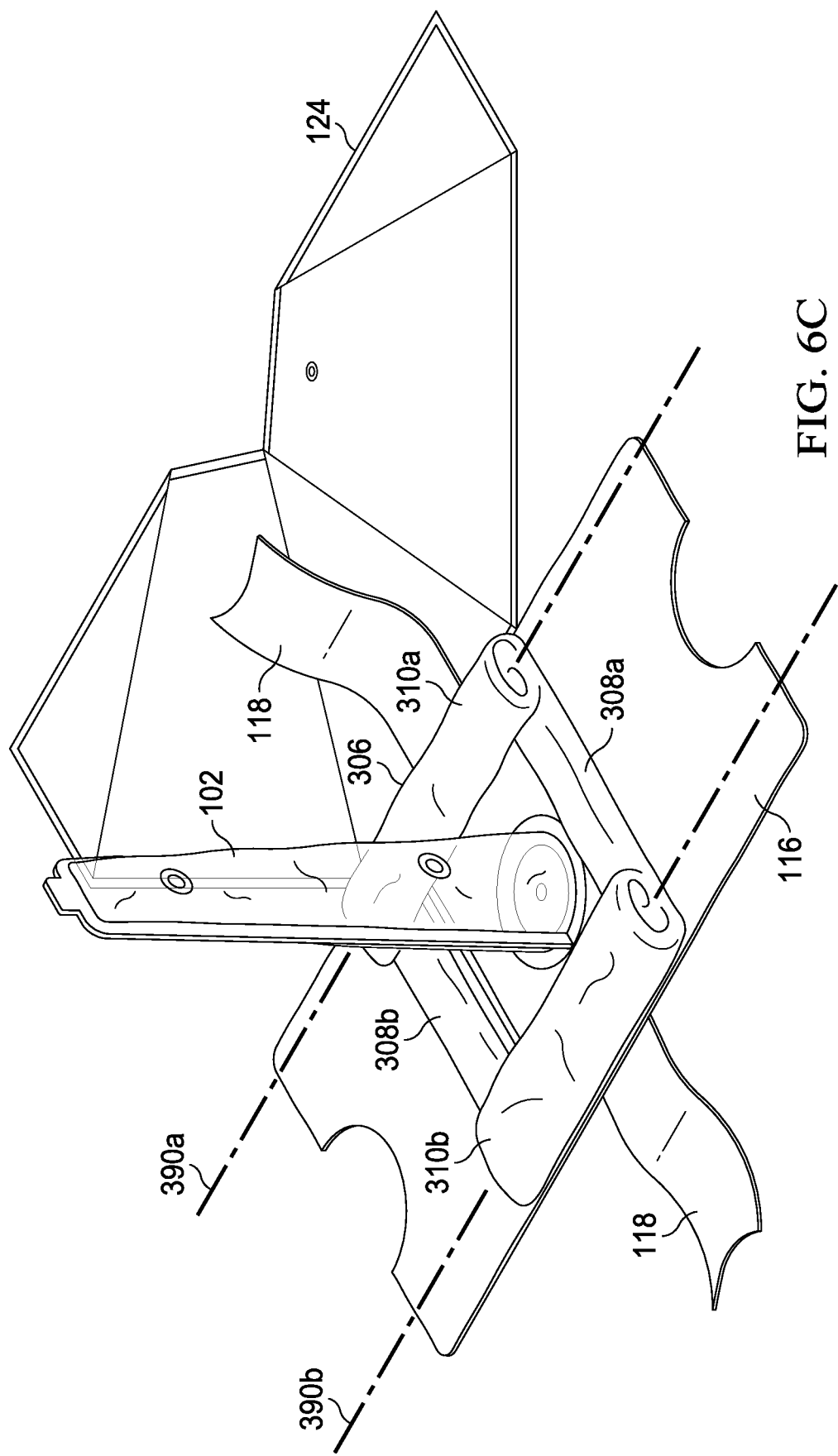

At step 522, the bifurcated seal ring is broken along the longitudinal perforations as shown in FIG. 6B. At step 524, the vacuum pack envelope is opened by grasping the now separated ring halves 127a and 127b and tearing through the longitudinal and the lateral seal closures, as shown in FIGS. 6B and 6C, thus exposing the surgical drape. Roll folds 310a and 310b and fan folds 308a and 308b may be seen in FIG. 6C. Preferably, roll folds 310a and 310b are generally aligned with axes 390a and 390b, respectively. It is preferred to have axis 390 generally parallel to axis 390b but efficacy of the device does not require it.

Figure 6D:
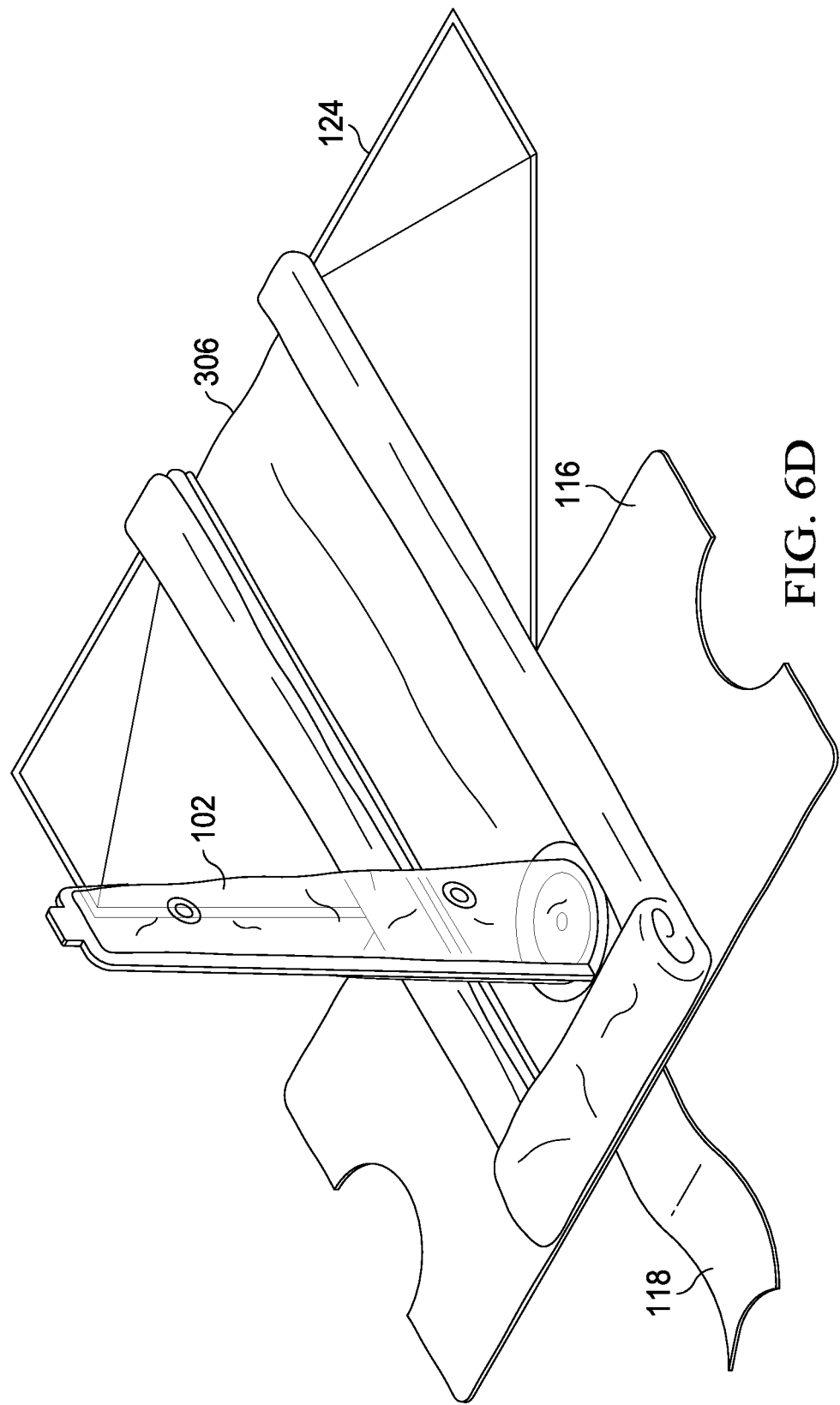
Figure 6E:
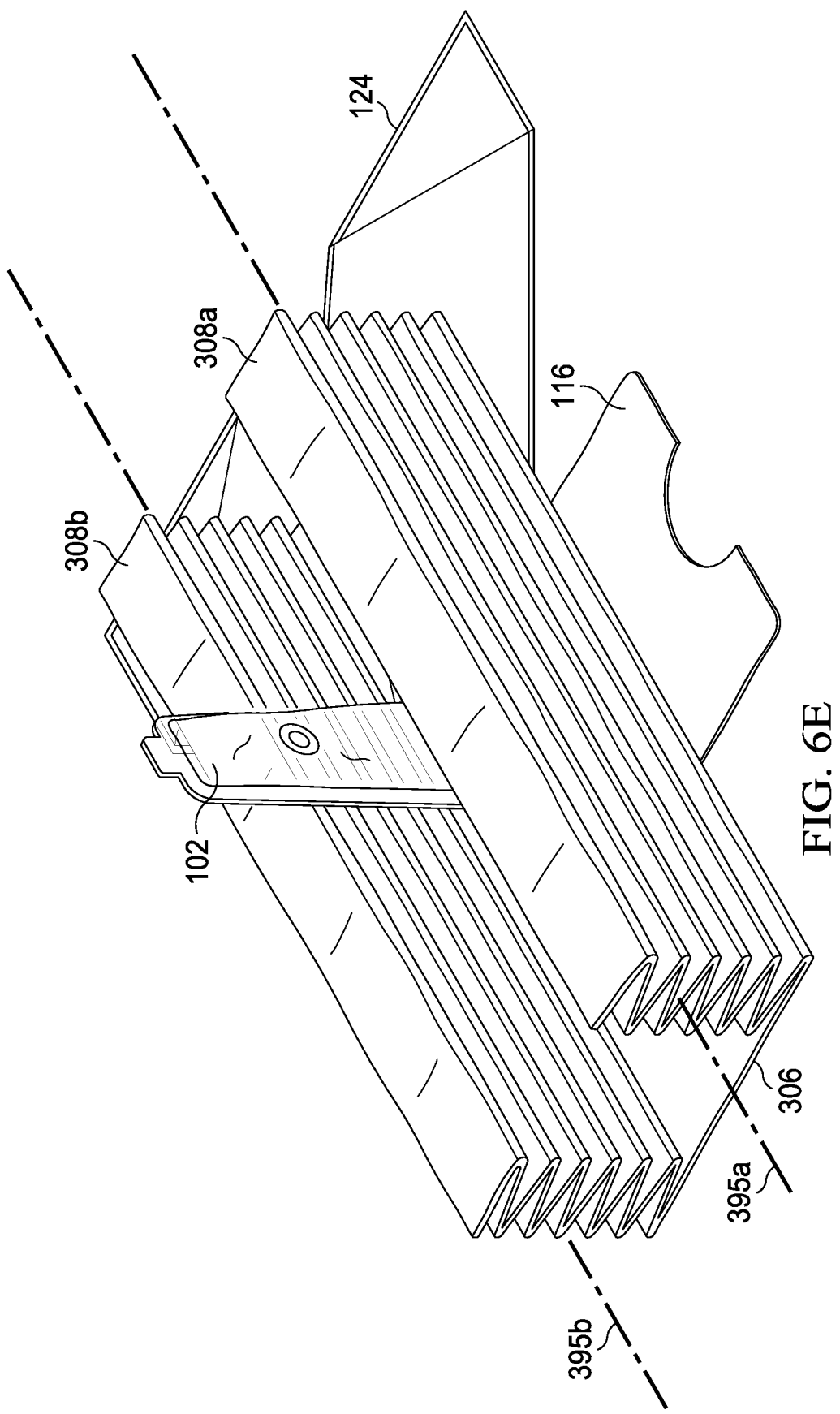
Figure 6F:
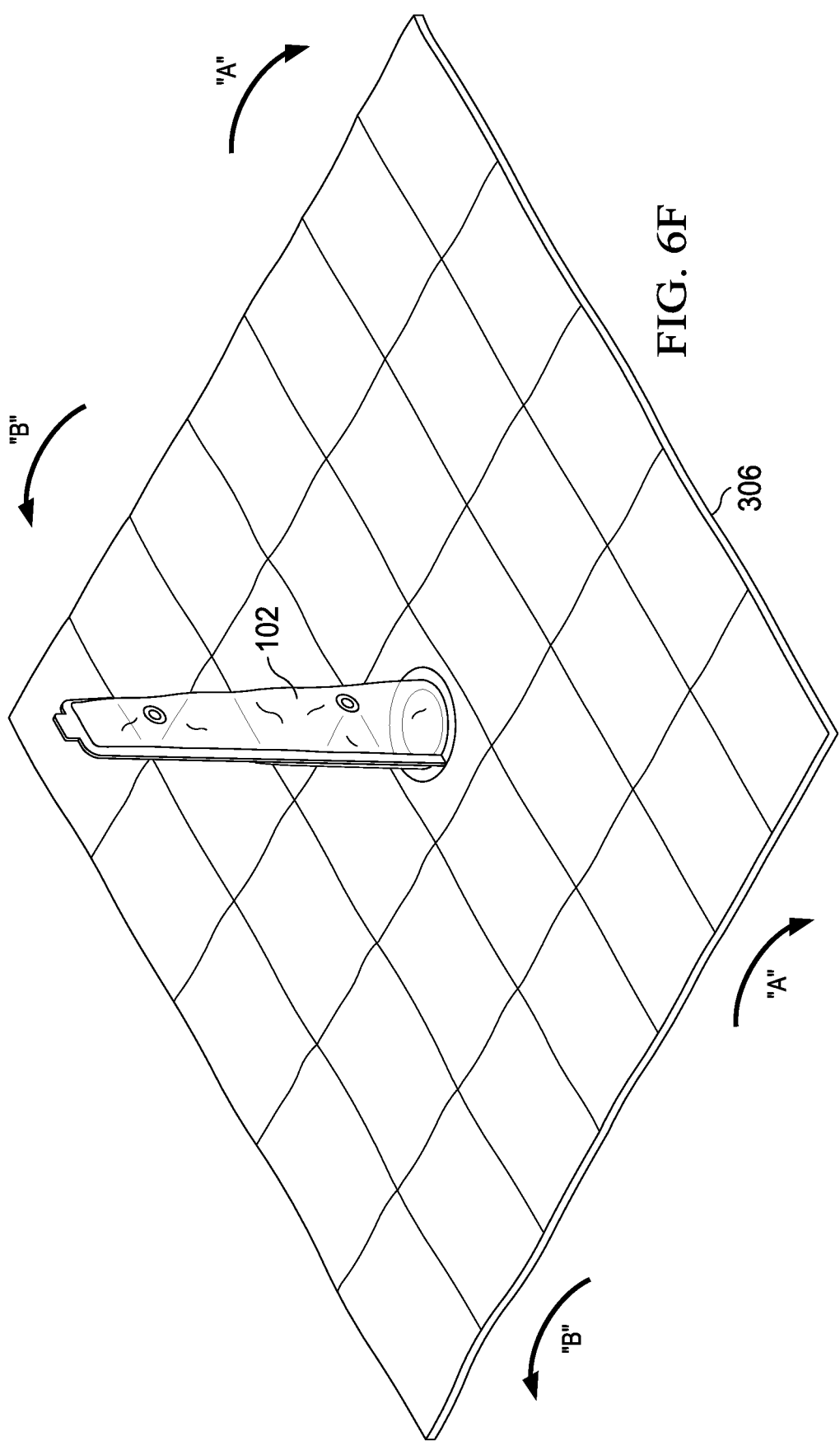

At step 526, the surgical drape is deployed by first unrolling the roll folds 310a and 310b, as shown in FIG. 6D, being careful to maintain the sterile field formed by the surgical drape. Fan folds 308a and 308b are then expanded along their fold lines, as shown in FIGS. 6E and 6F, thereby expanding the sterile field. As can be seen, fan fold 308a is generally aligned with axis 395a, and fan fold 308b is generally aligned with axis 395b. It is preferred to have axis 395a and 395b generally parallel, but efficacy of the device does not require it. As shown in FIG. 6F, the preferred order of deployment of the drape then includes unfurling the drape downward in the direction "A" to form a first section of the sterile field. Then, the drape is unfurled in the direction "B" forming a second section of the field.

At step 528, the flexible container is opened along lateral closures 106a and 106b, thereby exposing the extremity.

Referring to FIGS. 7A-7D, an example of placement and use of the device will be described. Other variations of the device can be placed on different extremities of the body.

Figure 7A:
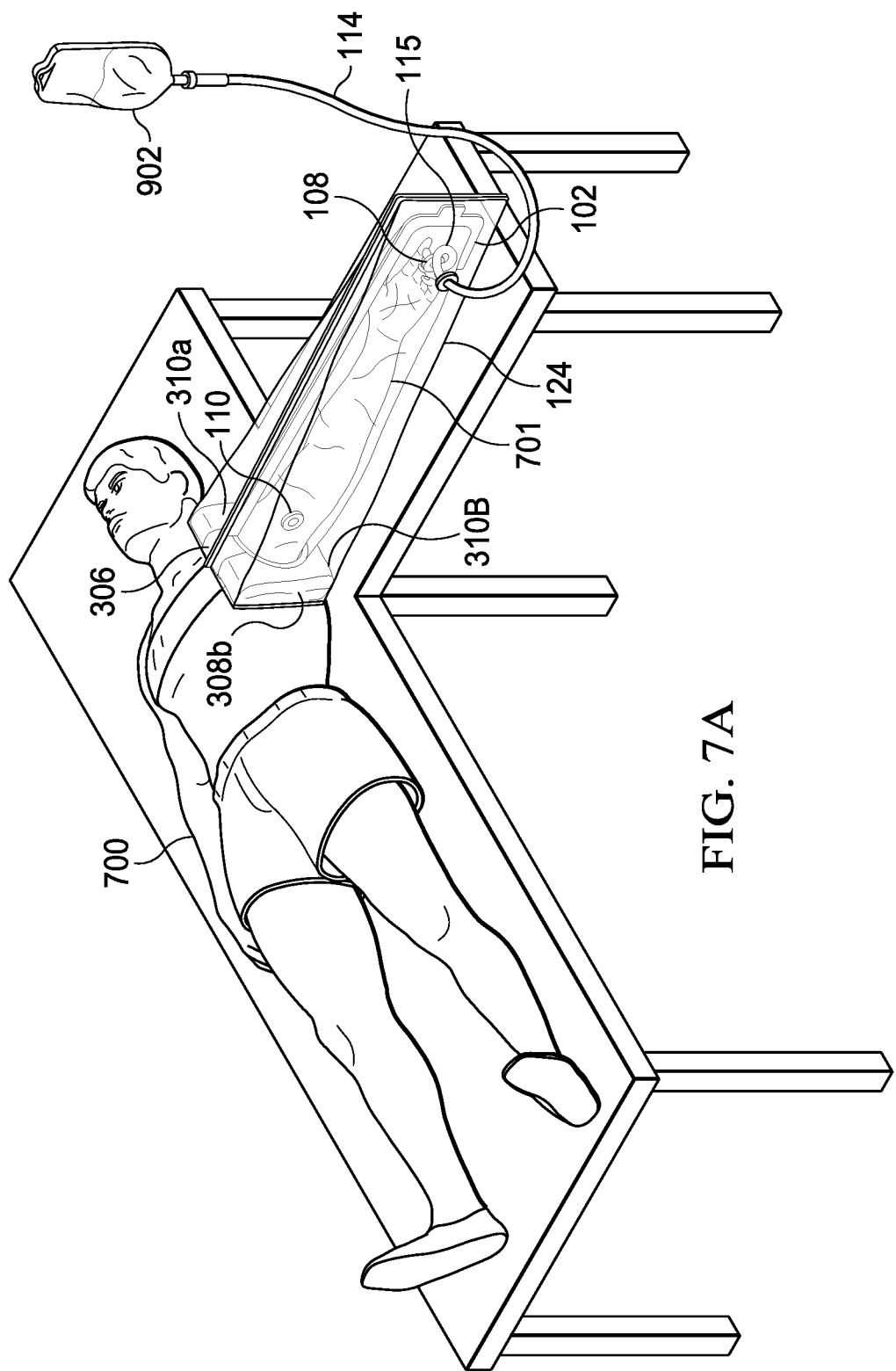
FIGS. 7A-7F show an example of a preferred embodiment of the invention in use.

In FIG. 7A, patient 700 is shown positioned with extremity 701 extended and the device attached to the patient's chest. Folded surgical drape 306 is preferably positioned against the patient with roll folds 310a and 310b generally parallel to the vertical axis of the patient. Fan folds 308a and 308b are shown adjacent to patient 700 and preferably positioned generally parallel to the sagittal axis. Use of the device on lower extremities will, of course, be recognized to require different positioning. In the case of lower extremities, the folded surgical drape is positioned with the roll folds generally perpendicular to the sagittal axis and the fan folds generally perpendicular to the vertical axis of the patient.

Extremity 701 is enclosed and sealed into flexible container 102 through orifice 114. Antiseptic is deployed into the flexible container from elevated antiseptic bag 902 through antiseptic deployment tube 904 and pigtail 115. The extremity may now be scrubbed without release of the antiseptic solution from the flexible container.

Figure 7B:
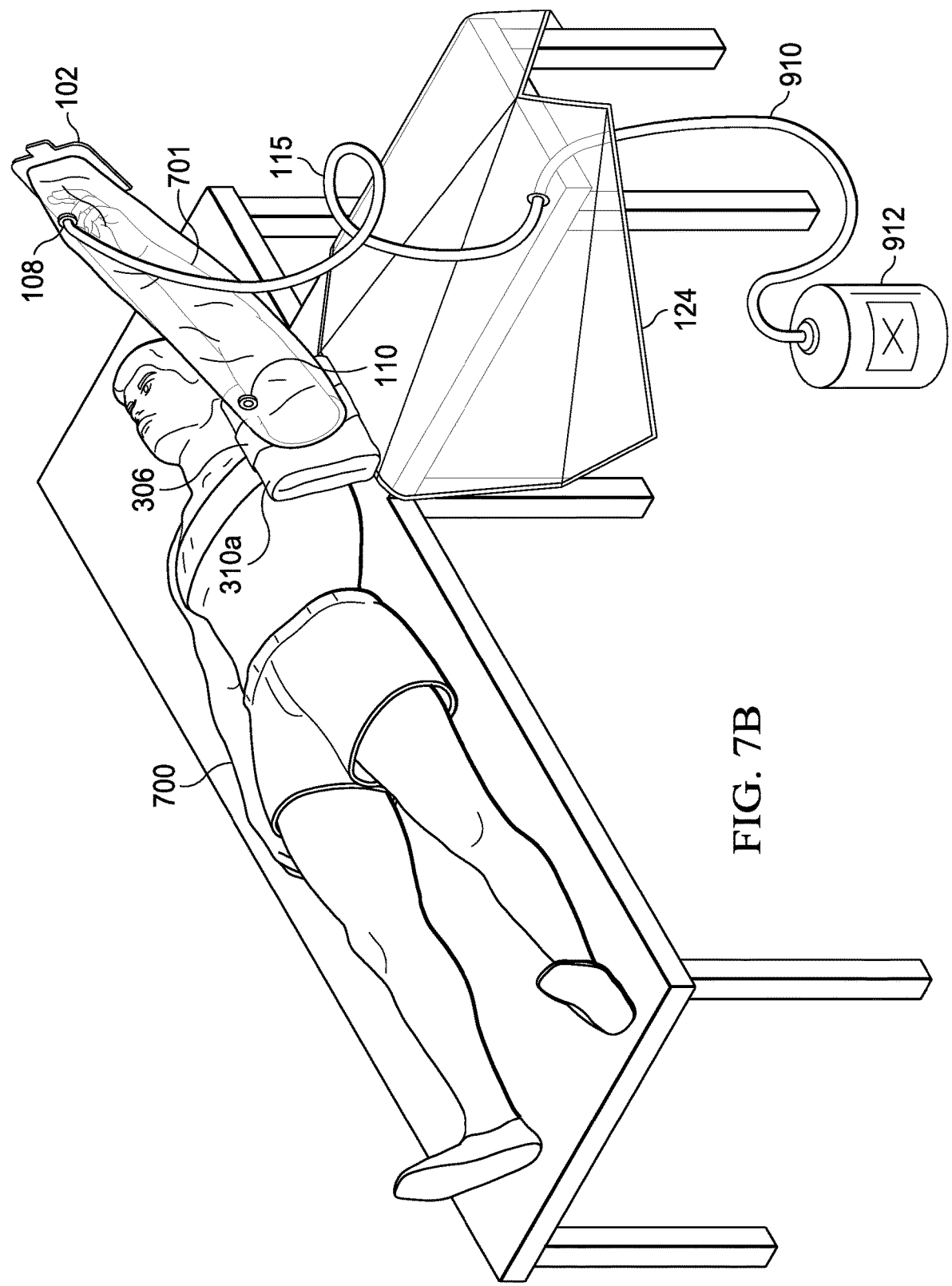

Referring then to FIG. 7B, patient 700 is shown positioned in the operating theater. Extremity 701 can be seen lifted into an elevated and extended position. The outer bag is shown open and properly positioned on the operating table below the extremity forming a sterile field. The antiseptic is drained from fluid port 108 through tube 910 and into container 912.

Figure 7C:
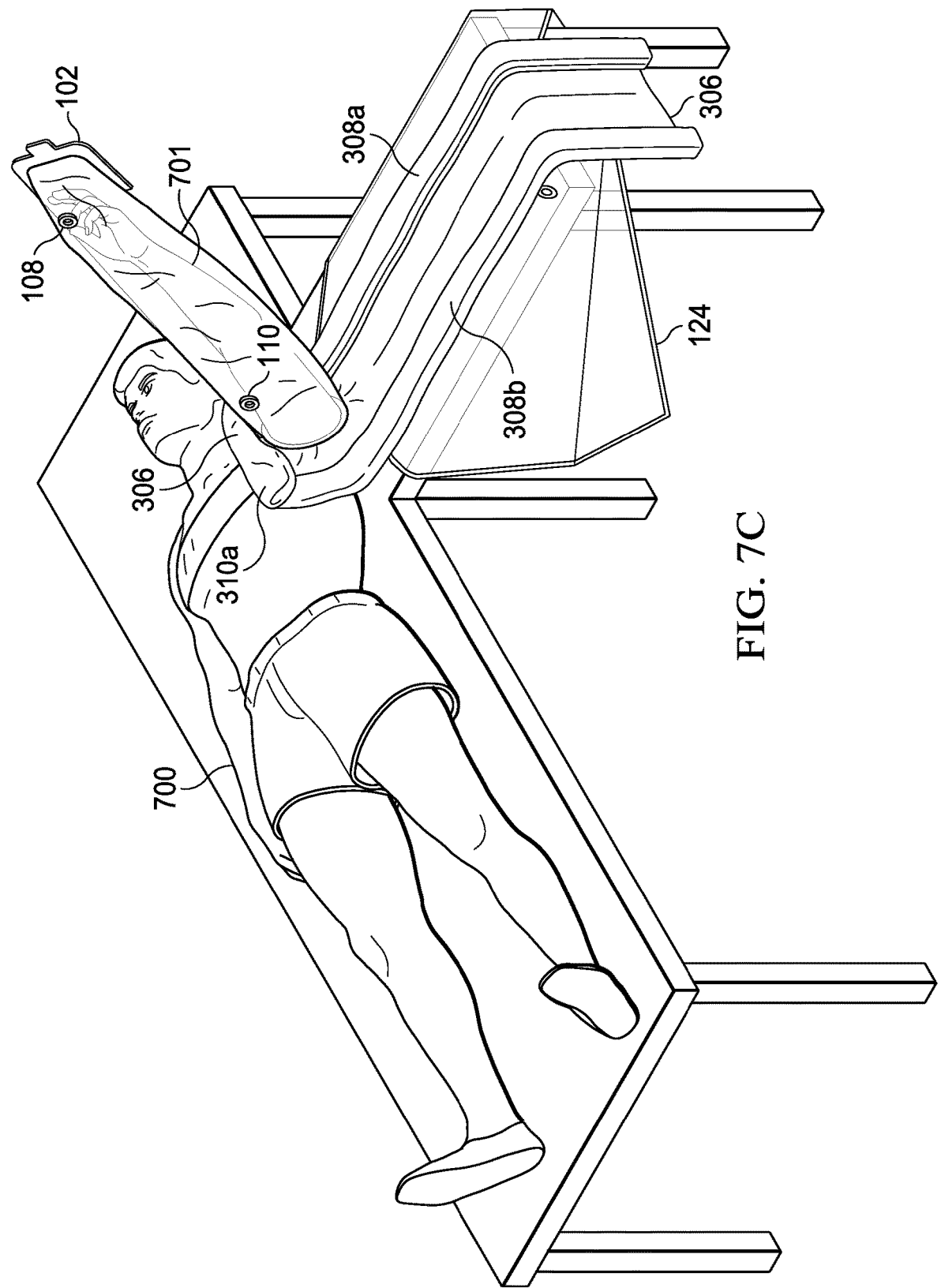

Referring to FIG. 7C, roll fold 310b is deployed along the left frontal horizontal axis. Similarly, roll fold 310a is then deployed along the right frontal horizontal axis. Deploying the roll folds in this manner allows two technicians to deploy the drape simultaneously, thereby saving time.

Figure 7D:
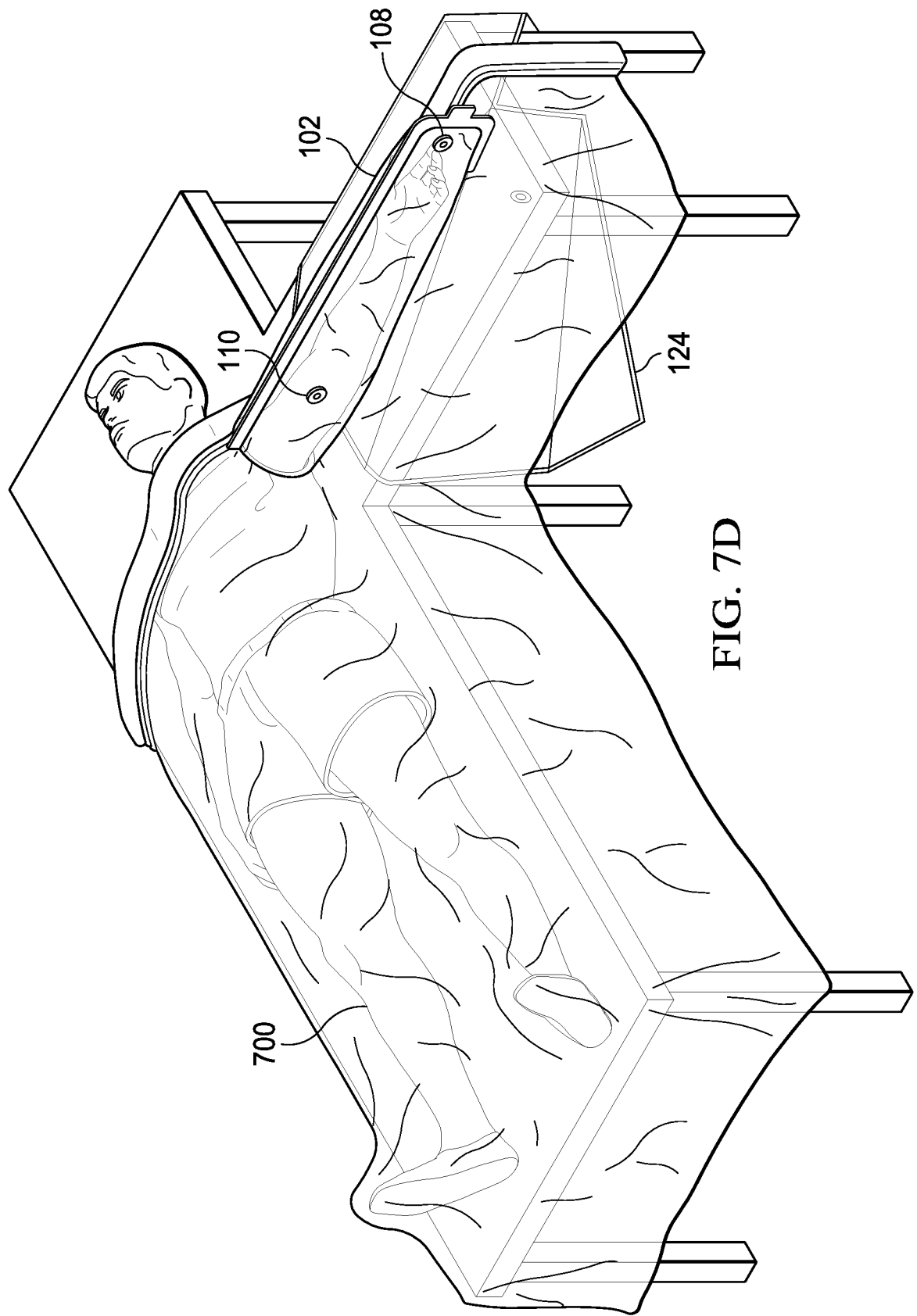
Figure 7E:
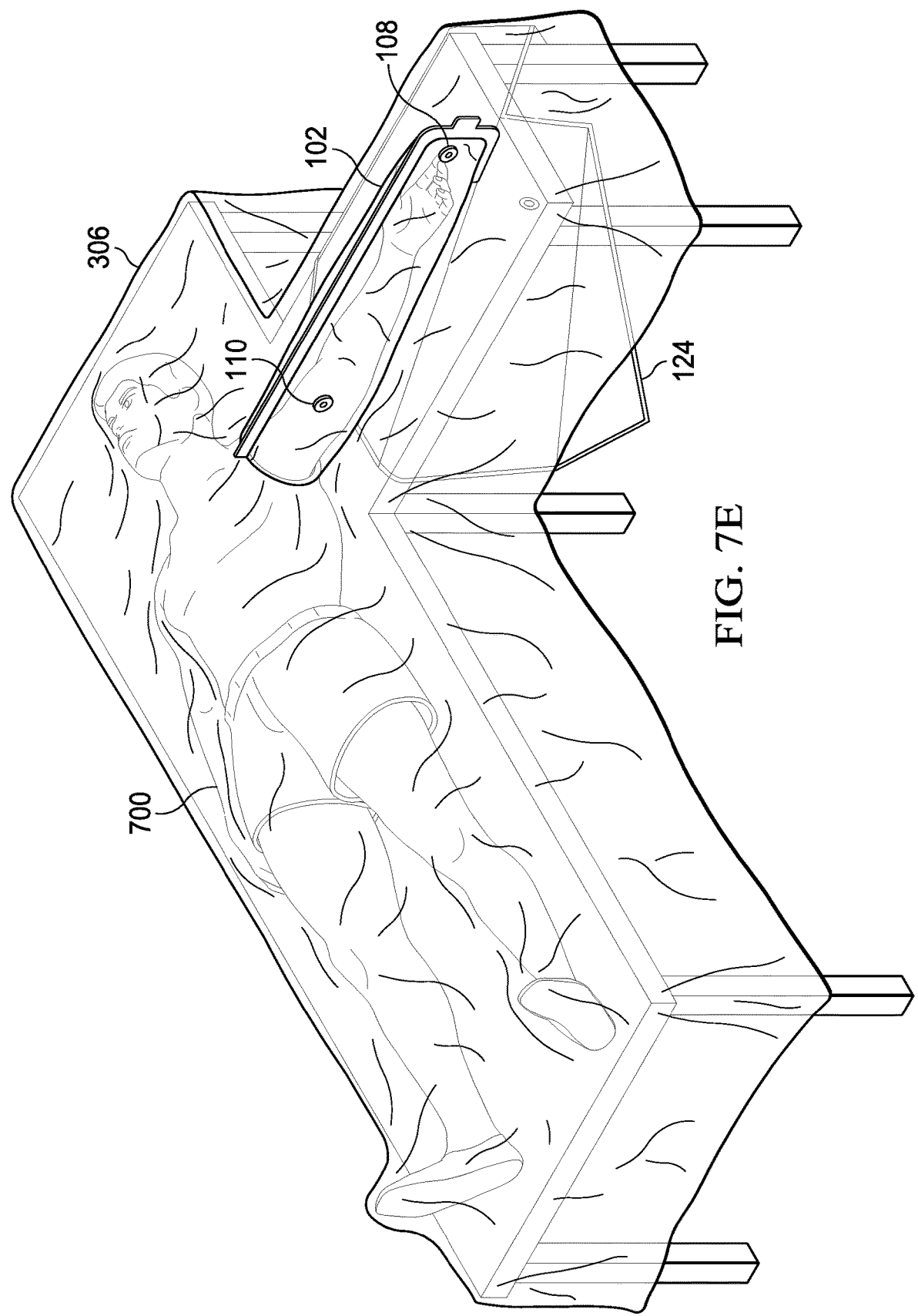
Figure 7F:
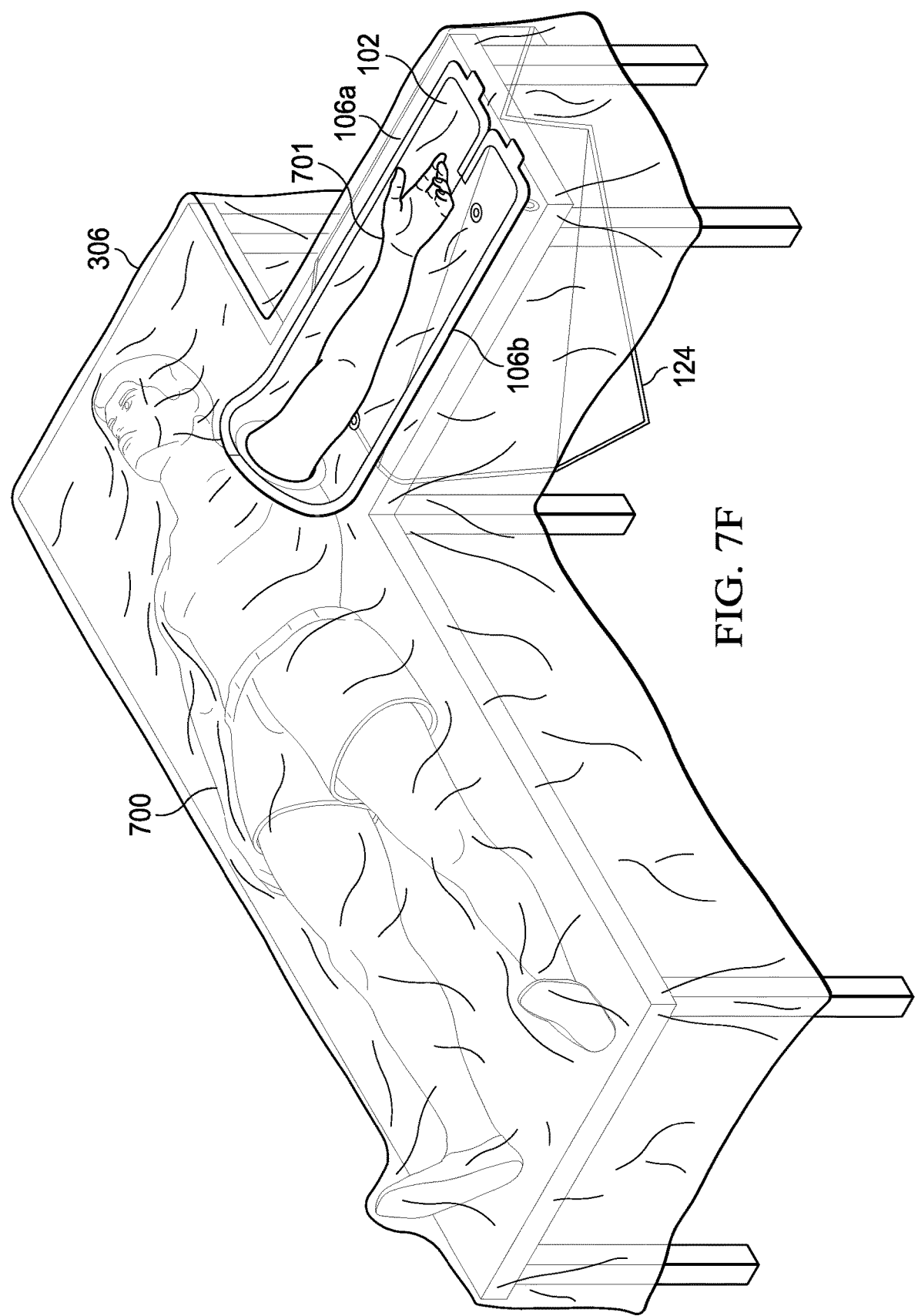

Referring to FIG. 7D, extremity 701 is lowered back to the sterile surface of the deployed surgical drape 306. Fan fold 308a is shown deployed toward the patient's inferior extremities along the vertical axis. Likewise, as shown in FIG. 7E, fan fold 308b is to be deployed in a superior direction along the vertical axis. Deploying the fan folds in this manner allows two technicians to be used simultaneously, thereby saving time.

As shown in FIG. 7E, in final preparation for surgery, flexible container 102 is opened along lateral closures 106a and 106b exposing extremity 701. It is important to observe that the fenestration in the surgical drape completely surrounds the extremity and that no folds or other openings in the surgical drape are present. Hence, the sterile field provided by the device, deployed in this manner, is far superior to the prior art.

Figure 8:
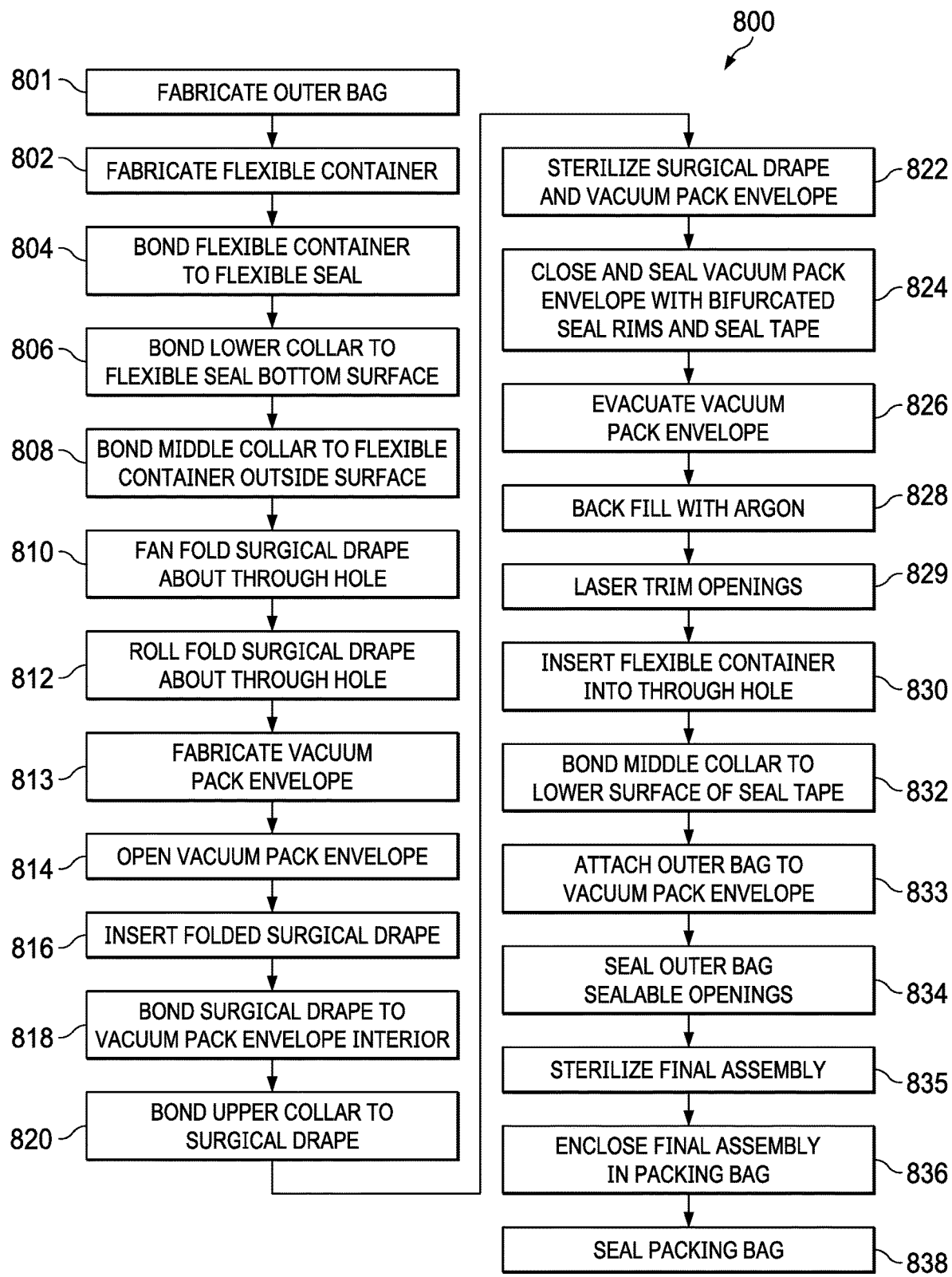
FIG. 8 is a flow chart of the steps of a preferred method of manufacture of the device.

Referring to FIG. 8, a preferred method of manufacture 800 of the device will be described.

At step 801, the outer bag is fabricated. Fabrication of the outer bag includes forming a plastic sheeting into the preferred shape by laser cutting according to an appropriate pattern and inductive welding the seams and lateral closure in place. Also, at this step, through hole seal 294 is inductively welded to one side of the bag. The through hole seal forms a ducted access to the interior of the outer bag and is sized to releasably seal against the drain tube. Also, at this step, the exterior surface of vacuum pack envelope subassembly 117 by a sealed permanent attachment such as a permanent rubber cement for inductive welding.

At step 802, the flexible container is fabricated, including forming the plastic sheeting into the appropriate shape by cutting according to a pattern and inductive welding the seams and attaching lateral closures 106a and 106b. Also, at this step, threaded base 109b and threaded base 111b are attached to through holes in the plastic sheeting which then form sealed and ducted access to the interior of the flexible container.

At step 804, the inside surface of the flexible container is bonded to flexible seal 112 along connection interface 113. Connection interface 113 in a preferred embodiment comprises the interior surface of the proximal end of the flexible container. In a preferred embodiment, the bond is formed by a flexible, permanent rubber cement as previously described.

At step 806, the lower collar is bonded to the bottom surface of the flexible seal.

At step 808, the middle collar is bonded to the exterior surface of the flexible container.

At step 810, the surgical drape is fan folded at two parallel sides of the surgical drape along parallel axes 395a and 395b, adjacent opening 305. In a preferred embodiment, the spacing of the fan folds is each approximately 10 cm. If the surgical drape has previously been sterilized, then care is taken at this step to not to contaminate any part of the surgical drape.

At step 812, each fan fold is roll folded along one of parallel axes 390a and 390b, adjacent opening 305.

At step 813, the vacuum pack envelope is fabricated, including forming the plastic sheeting into the appropriate shape by cutting according to a pattern and induction welding of the lateral and longitudinal closures. At this step, vacuum port 312 is also sealed to an opening and fixed in place. Optionally, the envelope may also be sterilized at this step.

At step 814, the vacuum pack envelope is opened along the seal closures. At step 816, the folded surgical drape is inserted into the vacuum pack envelope centering opening 305 around opening 303. In a preferred embodiment, the axes of roll folds 390a and 390b are positioned generally perpendicular to the longitudinal seal closures and parallel to the lateral seal closures. In like manner, the axes of fan folds 308a and 308b are positioned generally parallel to the longitudinal seal closures and generally perpendicular to the lateral seal closures. Positioning the folded drape in the envelope in this orientation is important because, when the vacuum pack envelope is opened, the likelihood of inadvertently deploying the roll folds before the envelope is completely removed is greatly reduced.

At step 818, the surgical drape is bonded to the vacuum pack envelope interior centering opening 305 to opening 303.

At step 820, the upper collar is bonded to the surgical drape centering opening 305 to opening 128. At step 822, the surgical drape and the vacuum pack envelope are sterilized.

At step 824, the vacuum pack envelope is closed and sealed by closing each of the sterile closures and then applying the bifurcated seal ring around opening 305 and then applying the seal tape to protect the seal closures.

At step 826, the vacuum pack envelope is evacuated through vacuum port 312. At step 828, the vacuum pack envelope may optionally be backfilled with Argon gas through the same vacuum port.

At step 829, the inside surfaces of each of openings 128, 353, 313, 305, 115 and 323 are laser trimmed to the same size and inductively scintered together. In this way, the edges of the various materials and components are smoothed to prevent inadvertent rupture of the flexible container during use.

At step 830, the flexible container is inserted into openings 128, 353, 313, 305, 115 and 323. At step 832, the middle collar is bonded to the lower surface of the seal tape.

At step 833, the outer bag is bonded to the exterior surface of the vacuum pack envelope.

At step 834, the entire final assembly is sterilized.

At step 836, the final assembly is enclosed in the packing bag and can also be vacuum sealed.

At step 838, the packing bag is sealed, preferably with an inductively welded closure. In alternate embodiments, the packing bag may be vacuum sealed.

The embodiments have been described in detail with particular reference to certain preferred embodiments thereof, but it will be understood that variations and modifications can be affected within the scope of the embodiments, especially to those skilled in the art.

The invention claimed is:

1. A device for applying an antiseptic solution to an extremity of a patient comprising:
a deployment package, having a central fenestration, containing a surgical drape;
a first flexible container, having an interior attached to the deployment package; and,
a second flexible container, extending through the central fenestration and into the interior of the first flexible container.

2. The device of claim 1 wherein the second flexible container further comprises:
a first opening; and,
a resilient gasket, having a central orifice, sealed to the first opening.

3. The device of claim 2 wherein the second flexible container further comprises:
a first lateral closure adjacent the resilient gasket;
a second lateral closure adjacent the resilient gasket; and,
wherein the first lateral closure is adapted to engage and seal with the second lateral closure.

4. The device of claim 3 wherein the second flexible container further comprises a fluid port.

5. The device of claim 1 wherein the deployment package further comprises a periphery; and,
wherein the first flexible container further comprises a first opening, releasably attached to the periphery.

6. The device of claim 5 wherein the first flexible container further comprises:
a first lateral closure, adjacent the first opening;
a second lateral closure, adjacent the first opening; and,
wherein the first lateral closure is adapted to engage and seal with the second lateral closure.

7. The device of claim 6 wherein the first flexible container is fixed to the periphery by a non-removable seam section.

8. The device of claim 1 wherein the first flexible container is ductedly connected to the second flexible container by a fluid transport tube.

9. The device of claim 1 wherein the deployment package further comprises:
a first lateral seal closure;
a first longitudinal seal closure intersecting the first lateral seal closure;
a second lateral seal closure; and,
a second longitudinal seal closure intersecting the second lateral seal closure.

10. The device of claim 9 further comprising:
a bifurcated seal ring, adjacent the central fenestration, affixed to the deployment package, and aligned with the first longitudinal seal closure and the second longitudinal seal closure.

11. The device of claim 10 further comprising a seal tape affixed to the deployment package, adjacent the bifurcated seal ring, and covering the first longitudinal seal closure and the second longitudinal seal closure.

12. The device of claim 11 further comprising a tie down strap affixed to the deployment package adjacent the seal tape.

13. The device of claim 1 wherein the surgical drape further comprises a pair of fan fold sections and a pair of roll fold sections.

14. The device of claim 13 wherein the pair of fan fold sections are generally perpendicular to the pair of roll fold sections.

15. The device of claim 1 wherein the deployment package is evacuated.

* * * * *